United States Patent
Srinivasan et al.

(10) Patent No.: US 7,670,633 B2
(45) Date of Patent: Mar. 2, 2010

(54) REMOVAL OF FIBER FROM GRAIN PRODUCTS INCLUDING DISTILLERS DRIED GRAINS WITH SOLUBLES

(75) Inventors: Radhakrishnan Srinivasan, Urbana, IL (US); Vijay Singh, Savoy, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 1265 days.

(21) Appl. No.: 11/180,475

(22) Filed: Jul. 13, 2005

(65) Prior Publication Data

US 2006/0040024 A1 Feb. 23, 2006

Related U.S. Application Data

(60) Provisional application No. 60/604,160, filed on Aug. 23, 2004.

(51) Int. Cl.
*A23L 1/216* (2006.01)
(52) U.S. Cl. .................. 426/482; 426/479; 426/618
(58) Field of Classification Search ............... 426/479, 426/482, 618
See application file for complete search history.

(56) References Cited

U.S. PATENT DOCUMENTS

| | | | |
|---|---|---|---|
| 2,808,929 A | 10/1957 | Fisher | |
| 3,587,980 A | 6/1971 | Ennigerloh et al. | |
| 4,181,748 A | 1/1980 | Chwalek et al. | |
| 4,632,833 A * | 12/1986 | Gannon | 426/242 |
| 5,063,078 A | 11/1991 | Foehse | |
| 5,725,901 A | 3/1998 | Fox | |
| 5,846,590 A * | 12/1998 | Malkki et al. | 426/443 |
| 6,083,547 A | 7/2000 | Katta et al. | |
| 6,254,914 B1 | 7/2001 | Singh et al. | |
| 6,624,300 B2 * | 9/2003 | Potter et al. | 536/123.12 |
| 2003/0104587 A1 | 6/2003 | Verser et al. | |
| 2003/0180415 A1 | 9/2003 | Stiefel et al. | |
| 2003/0232109 A1 | 12/2003 | Dawley et al. | |
| 2004/0101935 A1 | 5/2004 | Vasanthan et al. | |

OTHER PUBLICATIONS

PCT International Search Report, International Application No. PCT/US05/24959, dated Sep. 21, 2006, 3 pages.
41—R. Srinivasan et al., "Economics of fiber separation from distillers dried grains with solubles (DDGS) using sieving and elutriation," Cereal Chem. 83(4):324-330, 2006.
42—B. Sundberg et al., "Enrichment of mixed-linked (1-3), (1-4)-beta-D-glucans from a high-fibre barley-milling stream by air classification and stack-sieving," J. Cereal Science 21:205-208, 1995.

(Continued)

*Primary Examiner*—Anthony Weier
(74) *Attorney, Agent, or Firm*—Greenlee Winner and Sullivan, PC

(57) ABSTRACT

Methods, devices, and compositions relating to processed grain products are shown. An exemplary method shown is a fiber separation process for the ethanol industry corn products of Distillers Dried Grains (DDG) and Distillers Dried Grains with Solubles (DDGS) resulting from the widely used dry grind technology. The disclosed process and apparatus allows the removal and separate recovery of fiber-reduced DDG or DDGS products with expanded potential for use as a non-ruminant feed product in addition to the removal and separate recovery of a fiber-enriched product. The specific processes, devices, and compositions shown are readily adaptable to modern ethanol production plants.

21 Claims, 20 Drawing Sheets

OTHER PUBLICATIONS

AACC, Approved methods of the AACC, 10th ed, The American Association of Cereal Chemists, St Paul, MN, 2000, printout of Introduction and Table of Contents from website http://www.aaccnet.org/approvedmethods, Sep. 15, 2005, 16 pages.

AAFCO, Official publication of AAFCO, The Association of American Feed Control Officials Incorporated, Oxford, IN, 2002, p. 245.

Agblevor, F., Microbial production of xylitol from corn fiber, Industrial Bioprocessing 24:5, 2002.

AOAC, Official methods of the AOAC, 17th ed., The Association of Official Analytical Chemists, Gaithersburg, MD, 2003, printout of Table of Contents from website http://www.aoac.org/pubs/contents.html, Sep. 15, 2005, 2 pages.

Belyea, R. L. et al., Composition of corn and distillers dried grains with solubles from dry grind ethanol processing, Bioresource Technology 94:293-298, 2004.

Buchanan, C.M., High value products from corn fiber, Industrial Bioprocessing 24:3-4, 2002.

Buchheit, J. K., Production of ethanol, Rural Enterprise and Alternative Agricultural Development Initiative Report, Report No. 13, Jun. 2002.

Crosley, I., Classification overview, Malvern Instruments, Ltd., 2004.

Eckhoff, S.R. et al., A 100-g laboratory corn wet-milling procedure, Cereal Chemistry 73(1):54-57, 1996.

Grohmann, K. et al., Saccharification of corn fibre by combined treatment with dilute sulphuric acid and enzymes, Process Biochem. 32(5):405-415, 1997.

Huang, C. C., Air classifiers: How they work and how to select one, Powder and Bulk Engineering, Dec. 1996.

Lapedes, D.N., McGraw-Hill Dictionary of Scientific and Technical Terms, 2nd ed., McGraw-Hill, New York, NY, 1978, p. 110.

Linn, J. G. et al., Using distillers grains in dairy cattle rations, Proceedings of Professional Dairy Management Conference, Dubuque, IA, 1996.

Moreau, R. A. et al., Comparison of yield and composition of oil extracted from corn fiber and corn bran, Cereal Chemistry 76(3):449-451, 1999.

Moreau, R.A. et al., Phytosterols and phytostanols lower cholesterol, Inform 10:572-577, 1999.

National Research Council, United States-Canadian Tables of Feed Composition, 3rd Rev., Nat. Acad. Press, Washington, DC, 1982, p. 3-6.

National Research Council, Nutrient Requirements of Dairy Cattle, $6^{th}$ Revised Ed., National Academy Press, Washington, DC, 1988, p. 9.

RFA, U.S. fuel ethanol production capacity, Renewable Fuels Association, www.ethanolrfa.org/eth_prod_fac.html. Washington, DC, Sep. 2005

Richter, B., Using ethanol as an energy source, Letters to the Editor, Science 305:340, Jul. 16, 2004.

Singh, V. et al., Pretreatment of wet-milled corn fiber to improve recovery of corn fiber oil and phytosterols, Cereal Chemistry 80(2):118-122, 2003.

Singh, V., et al., Removal of fiber from distillers dried grains with solubles (DDGS) to increase value, Transactions of the American Society of Agricultural Engineers 45(2): 389-392, 2002.

Singh, V., et al., Modified dry grind ethanol process, Publication of the Agricultural Engineering Department, University of Illinois at Urbana-Champaign, UILU No. 2001-7021, Jul. 18, 2001.

Srinivasan, R. et al., Separation of fiber from distillers dried grains with solubles (DDGS) using sieving and elutriation, Cereal Chemistry 82(5):528-533, 2005.

Srinivasan, R. et al., A new process for removing fiber from distillers dried grains with solubles, ASAE Annual International Meeting, Tampa, Florida, Jul. 17-20, 2005, Paper No. 057044.

Synergy in Energy, Ethanol Industry Outlook 2004, Renewable Fuels Association, Feb. 2004.

Treybal, R.E., Mass-transfer operations, 3rd ed., McGraw-Hill, New York, NY 1980, pp. 346 and 488.

U. S. Department of Agricultural, National Agricultural Statistics Service, Iowa State Statistical Office, 2004 National Distillers Grains Summary Survey of Ethanol Producers, 2 pages.

U. S. Department of Energy, Office of Industrial Technologies, Energy Efficiency and Renewable Energy, Fractionation of corn fiber for production of polyols, Chemicals Project Fact Sheet, 2 pages, Feb. 1999.

van Soest, P. J. et al., Symposium: Carbohydrate methodology, metabolism, and nutritional implications in dairy cattle, Methods for dietary fiber, neutral detergent fiber, and nonstarch polysaccharides in relation to animal nutrition, J. Dairy Sci. 74:3583-3597, 1991.

Wu, Y.V. et al., Corn distillers' dried grains with Solubles and corn distillers' dried grains: Dry fractionation and composition, Journal of Food Science 47:1155-1157,1180, 1982.

Wu, Y.V. et al., Simple dry fractionation of Corn Distillers' Dried Grains and Corn Distillers' Dried Grains with Solubles, Cereal Chemistry 63(1):60-61, 1986.

Zhang, Y. et al., Modeling and sensitivity analysis of dust particle separation for uniflow dedusters, from website visited Jun. 2005 at: http://www.age.uiuc.edu/bee/RESEARCH/Deduster/dedpaper1.html.

C. Martinez-Amezcua et al., "Nutritional characteristrics of corn distillers dried grains with solubles as affected by the amount of grains versus solubles and different processing techniques," Poultry Science 86:2624-2630, 2007.

C. M. Parsons et al., "Nutritional value of conventional and modified DDGS for poultry," Multi-State Poultry Nutrition and Feeding Conference, 2006, 7 pages.

R. Srinivasan et al., "Fiber separated from distillers dried grains with solubles as a feedstock for ethanol production," Cereal Chemistry 84(6):563-566, 2007.

R. Srinivasan et al., "Phytosterol distribution in fractions obtained from processing of distillers dried grains with solubles using sieving and elutriation," Cereal Chemistry 84(6):626-630, 2007.

R. Srinivasan et al., "Pericarp fiber separation from corn flour using sieving and air classification," Cereal Chemistry 85(1):27-30, 2008.

R. Srinivasan et al., "Fiber separation from distillers dried grains with solubles using a larger elutriation apparatus and use of fiber as a feedstock for corn fiber gum production," Biological Engineering 1(1):39-49, 2008.

R. Srinivasan et al., "Separation of fiber from distillers dried grains (DDG) using sieving and elutriation," Biomass and Bioenergy 32:468-472, 2008.

R. Srinivasan et al., "Physical properties that govern fiber separation from distillers dried grains with solubles (DDGS) using sieving and air classification," Separation and Purification Technology 61:461-468,2008.

* cited by examiner

REMOVAL OF FIBER FROM GRAIN PRODUCTS INCLUDING DISTILLERS DRIED GRAINS WITH SOLUBLES

CROSS-REFERENCES TO RELATED APPLICATIONS

This application claims the benefit of U.S. Provisional Application No. 60/604,160 by Srinivasan and Singh, filed Aug. 23, 2004. Each application(s) is incorporated herein by reference in entirety.

STATEMENT REGARDING FEDERALLY SPONSORED RESEARCH OR DEVELOPMENT

Not applicable

BACKGROUND OF THE INVENTION

A significant agricultural commodity, corn (maize) is processed for several purposes including industrial uses in addition to human and animal consumption. An increasingly important industrial use of corn is the production of ethanol which is in turn used, for example, as a fuel. Indeed, ethanol production from corn is expected to rise rapidly, with projections indicating a doubling of production capacity within the next few years.

A widespread method of ethanol production utilizes the Dry Grind process and modified versions thereof; see FIGS. 1 and 2. Ethanol producers often prefer the Dry Grind process to an alternative method known as Wet Milling (FIG. 3) due to the simplicity, low initial capital investment, and lower operating costs associated with Dry Grind. The Dry Grind process is currently estimated to yield about 70% of the ethanol produced in the United States. These trends of increased ethanol production and acceptance of Dry Grind are forecast to continue.

Corn can be described as comprising several components. The four main components include starch, also referred to as the carbohydrate or sugar component; protein; fat, also referred to as oil; and fiber. In the Dry Grind process, starch is converted to ethanol. First, the corn is ground into corn flour. Next, water is added to the corn flour, and the resulting slurry is treated in the presence of enzymes to convert the sugars to glucose. Glucose is fermented using yeast to produce crude ethanol. The crude ethanol-water mixture is treated by distillation, yielding purified ethanol.

From the distillation step, the solids or "grains" coming out of the distilling column are called Distillers Grains. The water component resulting from the distillation column is evaporated and the resulting "solubles" are mixed with the Distillers Grains; this combination is conventionally known as Distillers Grains with Solubles. Alternatively, the Distillers Grains are not mixed with the Distillers Solubles. Finally, the Distillers Grains or Distillers Grains with Solubles are dried, generating Distillers Dried Grains (DDG) or Distillers Dried Grains with Solubles (DDGS). DDGS consists largely of corn minus the starch component; in other words, DDGS has the remaining components of protein, fat, fiber, and some unconverted starch. Physically, it is a solid powdery or aggregate material with color hues ranging from a bright golden yellow to brown.

Dry Grind processing in the ethanol production industry thus yields DDGS as a major byproduct. Directly correlating with the increase in ethanol production, the supply of DDGS as a commodity will likely increase proportionately. As a commodity, DDGS has constrained economic value. For example, the typically high fiber content of DDGS restricts its applicability as a feed product. DDGS is highly suitable as an animal feed for ruminant animals such as cattle which can naturally digest the fiber. Non-ruminant animals, however, are generally less able to digest high fiber DDGS. DDGS as commercially produced is also found to be variable in its nutrient composition such as protein, fat, fiber, ash, or starch content (see Belyea, 2004). This variability can diminish the value of DDGS when business consumers consider certain criteria for a feed product to be of importance such as minimum protein and/or fat content proportions.

Attempts have been made to improve processes and products of ethanol production from corn. See U.S. Pat. No. 6,254,914 by Singh et al., issued Jul. 3, 2001; United States Patent Applications 20030104587 by Verser et al., published Jun. 5, 2003; 20030180415 by Stiefel et al., published Sep. 25, 2003; and 20030232109 by Dawley et al., published Dec. 18, 2003.

In Singh, et al., 2002, the possibility of using air aspiration to remove fiber from DDGS was investigated. A kilogram sample of DDGS was placed on a 20-mesh screen and aspirated with an air jet at a pressure of approximately 2.8 atmospheres using a procedure similar to that of Eckhoff et al., 1996. The study showed limited success for aspiration in recovering fiber from DDGS and in recovering phytosterol compounds which are plant sterols that may be useful in lowering cholesterol levels. Aspirating DDGS samples produced by the dry-grind ethanol process did not yield an aspirated fraction that was significantly enriched in phytosterols. Aspiration of DDGS resulted in enrichment of oil and protein content and reduction of the neutral detergent fiber in the "residual" DDGS fraction (original DDGS after the removal of the aspirated fraction; note that terminology in Singh et al., 2002 may not necessarily correspond to present usage herein). The reduction in fiber content of this residual DDGS, however, was not found to be large enough to make a practical feedstuff for non-ruminants because the fiber levels were significantly above levels typically found in non-ruminant diets (Singh et al., 2002).

An invention that improves the economic value of grain products such as DDG or DDGS is highly desirable. DDGS can be improved by one or more of decreasing the fiber content, enriching the protein and/or fat content, and standardizing the nutrient content of the commodity. Reduction of the high fiber content can open up the use of DDG or DDGS as a feed product to non-ruminant animals and help maintain the supply and demand balance of the commodity. As a side benefit, a fiber-enriched product of the invention can itself contribute value to an ethanol production plant as an additional useful product of the DDGS processing and ultimately of corn. Some examples of valuable products potentially available from the fiber-enriched products include corn fiber gum and corn fiber oil. The phytosterol-containing oil in the corn fiber (corn fiber oil) has potential use as a natural low-density lipoprotein (LDL) lowering nutraceutical (see Moreau R A et al., 1999, Cereal Chemistry 76(3):449-451; Singh V et al., 2003, Cereal Chemistry 80(2):118-122). A fiber-enriched product can also be useful for dietary needs or as a laxative.

The present invention addresses problems related to the state of the art in agricultural technologies involving grain products. Among other items, the invention addresses the ethanol industry byproducts of DDG and DDGS in particular.

SUMMARY OF THE INVENTION

The following definitions are applicable.

When used herein, the term "classifying" refers to a separation or differentiation of a material into fractions based on one or more characteristics of a particle or aggregate of the material such as density, shape, size, and/or weight. The material can be heterogeneous with respect to the components of composition of material; for example, the material can have components of fiber, protein, fat, and starch. Alternatively, the material can be homogenous or heterogeneous regarding the composition but heterogeneous in another aspect, namely that particles of the material can vary in size, shape, density, electrostatic charge, or other parameter. In an example, the material is substantially all fiber; however, the fiber component can have larger and smaller fiber particles. The term is intended to broadly encompass and relate to classification systems, processes, and devices as known in the art. In a preferred embodiment, the term refers to air classification. In a specific embodiment, a subset of classifying is elutriation. In a specific embodiment, a subset of classifying is aspiration.

When used herein, the term "elutriation" refers to a purification, separation, or removal process. In an embodiment, the process can effect the separation of particles. In a preferred embodiment, the separation can be on the basis of one or more physical properties such as particle size, density, shape, weight, or other property. In a particular embodiment, such a process can be achieved by a washing or treatment with a fluid flow, where a fluid can be air. In a preferred embodiment, the process utilizes ambient air to separate a starting material into heavy and light fractions.

When used herein, the term "fraction" refers to a separated or differentiated portion of a starting substance. The term is intended to encompass a yet further differentiated portion of a fraction or subfraction.

When used herein, the term "heavier fraction" or "heavy fraction" can generally be understood by one of ordinary skill in the art. In an embodiment, the term refers to a material which can or does tend to settle downwards during a classification process. In a particular embodiment, the material settles at the bottom of an air elutriation column. Other equivalent terms in an embodiment can be referred to as heavy material, heavier material, or residual fraction.

When used herein, the term "lighter fraction" or "light fraction" can generally be understood by one of ordinary skill in the art. In an embodiment, the term refers to a material which can or does tend to be carried upwards during a classification process. In a particular embodiment, the material is carried by air towards the top of an elutriation column in an elutriation process. Other equivalent terms in an embodiment can be referred to as light material or lighter material. Another equivalent term in an embodiment is fiber fraction, indicating an instance where such fraction has an enriched fiber content relative to an earlier material.

When used herein, the term "sieving" refers to a separation process which is based on the difference in the size of particles of a material. In a particular embodiment, the process uses a mechanical sieve or screen. For example, a sieve can be in the form of a regular or irregular mesh, a perforated solid surface, a three-dimensional matrix, or a column of differential porosity. The term encompasses a process separating a larger or coarser particle from a smaller or finer particle. In an embodiment, separation is achieved with the assistance of equipment using vibratory motion.

When used herein, the term "Distillers Dried Grains with Solubles" or DDGS broadly refers to a non-fermentable byproduct of the corn kernel. In an embodiment, the term includes DDGS such as conventionally generated by the ethanol production industry (see FIG. 1). When produced from corn, DDGS is generally a combination of protein, fat, fiber, and unconverted starch. The term is intended to encompass modified DDGS such as generated from the modified dry grind ethanol process (see FIG. 2). The term can be interpreted as understood in the art and is intended to encompass definitions such as the feed ingredient definition according to the Association of American Feed Control Officials, including the product obtained after removal of ethyl alcohol by distillation from the yeast fermentation of corn by condensing and drying at least three-fourths of the solids of the resultant whole stillage. When used herein, note that DDGS is a processed corn product itself while serving as a starting material for further processing to generate additional processed corn products.

When used herein, the term "Distillers Dried Grains" or DDG broadly refers to a non-fermentable byproduct of the corn kernel. In an embodiment, the term includes DDGS such as conventionally generated by the ethanol production industry. The term can be interpreted as understood in the art and is intended to encompass definitions such as the feed ingredient definition according to the Association of American Feed Control Officials, including the material obtained after the removal of ethyl alcohol by distillation from the yeast fermentation of corn by separating the resultant coarse grain fraction of the whole stillage and drying it.

When used herein, the term "processed grain product" refers to a material that is available for consumption by animals or humans and for industrial purposes. In an embodiment, the term includes DDGS and DDG of the corn ethanol production industry. In other embodiments, the term includes legumes (e.g. soybeans), barley, wheat, sorghum, and other materials (e.g. other oilseeds).

When used herein, the term "enriched" refers to an attribute of an intermediate output or ending material that is at least partially increased in a component relative to a starting material. For example, an output material can be fiber-enriched, protein-enriched, or fat-enriched.

When used herein, the term "reduced" refers to an attribute of an output material that is at least partially decreased or depleted in a component relative to a starting material. For example, an output material can be fiber-reduced, protein-reduced, or fat-reduced.

When used herein, the term "Residual DDGS" or "Residual product" refer in an embodiment to an output material with a fiber content amount that is lesser than that found in an original DDGS material from which the output is derived. In a specific embodiment, this material can have expanded use as a feed product, for example in non-ruminant animals in addition to ruminant animals.

When used herein, the term "fiber-enriched fraction" or "fiber-enriched product" refer in an embodiment to an output material with a fiber content amount that is greater than that found in an original DDGS material from which the output is derived.

When used herein, the term "output" or "output product" refers generally to a product material generated from an input or starting material or from a previous output material. In an embodiment, an output can be a fraction. In an embodiment, an output can be an intermediate stage product or an end or final product. In a particular embodiment, the term can refer to either residual DDGS or a fiber-enriched fraction.

When used herein, the term "phytosterol" refers to one or more plant-based sterol compounds. The term is intended to be understood as known in the art and can encompass the definition by the National Cancer Institute (http://www.cancer.gov/dictionary/), including a plant-based compound that can compete with dietary cholesterol to be absorbed by the intestines, resulting in lower blood cholesterol levels; phytosterols may have some effect in cancer prevention.

The following abbreviations are applicable. DDGS, Distillers Dried Grains with Solubles; ADF, acid detergent fiber; NDF, neutral detergent fiber.

In an embodiment, the invention provides a method for processing an agricultural grain product by a combination of two separation techniques, classifying and sieving. One or more fractions produced by the method can be used as independent products or variously combined. In an embodiment, a desired fraction or combination of fractions can be determined so as to yield a high, optimal, or maximal economic return based on a projected or actual commercial market value for a given fraction or combination of fractions.

In an embodiment, the invention provides a method for processing an agricultural grain product by a single separation technique. In a particular embodiment, the technique is classifying or sieving.

In an embodiment, the processing methods of the invention can include a step of grinding or milling to generate a material with certain size parameters, e.g. a uniform size or a material with an average particle size or threshold particle size. In a particular embodiment, one or more size parameters are selected so as to facilitate separation such as by size. For example, grinding or milling is used to prepare a material for sieving or another separation technique. In an embodiment, the milled or ground material is subjected to air classification alone in order to separate the fiber. In an embodiment, upstream processing in dry grind plant is carried out such that size and characteristics of DDGS facilitate use of only one separation technique to separate fiber from DDGS. In an embodiment, grinding/milling of corn, size of syrup balls, and other governing parameters in the process are controlled such that a single separation technique of either air classification or sieving is effective in separating fiber from DDGS. In an embodiment, air classification, sieving or a combination of the two is used to separate fiber from milled corn flour in the upstream of the dry grind processing instead of separating fiber from DDGS.

In an embodiment, the invention provides a method of separating a material by electrostatic precipitation. For example, a first particle with a first size and first electrostatic charge can be separated from a second particle with a second size and second electrostatic charge. In an embodiment, the first size of the first particle is larger than the second size of the second particle, and vice versa in another embodiment (likewise for the electrostatic charge). The size and charge parameters along with other physical properties can be exploited to facilitate separation of the material. An electrostatic charge can be induced in a classifying column, sieving device, or gravity flow slide/incline (wherein the slide/incline can be porous to function simultaneously as a sieve).

The present inventors have surprisingly discovered that the invention can be specifically applied to solving the problem of how to increase the utilization of a coproduct of the ethanol industry, DDGS. In the example of DDGS, it has been found that the fiber components of the DDGS are generally less dense than the non-fiber components (here, 'non-fiber' does not necessarily mean completely devoid of fiber for a given particle or aggregate as found in commercial of DDGS). Hence, when air is passed through the DDGS, a substantial portion of the fiber component is carried along by the air. Some non-fiber, however, also can get carried along by the air because the forces experienced by large-sized fiber particles and small-sized non-fiber particles are the same. The non-fiber material can then be subjected to a further purification step of separation by size of particles. In an application of the invention, elutriation and sieving conditions can be adjusted to enhance a desired yield or degree of purity for a fiber or non-fiber output fraction. The availability of these new output fractions from DDGS thus expands its utilization as a coproduct of the ethanol industry.

The invention provides a method of generating at least one fiber-enriched fraction and at least one fiber-reduced fraction from a processed grain product starting material, comprising: a) classifying said grain product into a first fraction and a second fraction, wherein said first fraction has a lighter material and said second fraction has a heavier material reduced in fiber relative to said starting material; and b) separating by size said first fraction into first and second subfractions, wherein said first subfraction has a larger particle size and is enriched in fiber relative to said starting material and said second subfraction has a smaller particle size and is reduced in fiber relative to said starting material; thereby generating at least one fiber-enriched fraction and at least one fiber-reduced fraction from a processed grain product. In an embodiment, the invention provides this method further comprising combining said second fraction with said second subfraction, thereby forming a combined material reduced in fiber relative to said starting material.

In an embodiment, the method generates at least one fiber-reduced fraction enriched in protein content, fat content, or both protein and fat content.

In a preferred embodiment, the processed grain product is Distillers Dried Grains with Solubles, DDGS. In another preferred embodiment, the processed grain product is Distillers Dried Grains, DDG. In an embodiment, the processed grain product is derived from one or more of legumes (e.g. soybeans), barley, wheat, and sorghum.

In an embodiment where the processed grain product is DDGS or analogous material for other products, the methods, compositions, and devices of the invention are applicable for said DDGS or analogous material produced by any modification in the beginning of a dry-grind process. Exemplary modifications include a quick germ process, a quick fiber process, an enzymatic wet-milling process, the use of new enzymes, combinations of the foregoing, and other upstream changes in the dry-grind process.

In embodiments of methods of the invention, classifying uses gravity air elutriation. In embodiments, separation based on particle size difference is performed by sieving.

The invention provides a method of generating at least one fiber-enriched fraction and at least one fiber-reduced fraction from a processed grain product starting material, comprising: a) separating by size said grain product into a first fraction and a second fraction, wherein said first fraction has a larger particle size and said second fraction has a smaller particle size; and b) a first classifying, wherein said first fraction is classified so as to yield a first subfraction of a lighter material enriched in fiber relative to said starting material and a second subfraction of a heavier material reduced in fiber relative to said starting material; thereby generating a fiber-enriched fraction and a fiber-reduced fraction from a processed grain product. In an embodiment, this method comprises combining said second fraction of smaller particle size and said second subfraction, thereby forming a combined material reduced in fiber relative to said starting material.

In an embodiment, the invention provides a method comprising a second classifying, wherein said second fraction (smaller particle size) is classified so as to yield a third subfraction of a lighter material enriched in fiber and a fourth subfraction of a heavier material reduced in fiber. In a particular embodiment, this method further comprises combining said first subfraction with said third subfraction, thereby forming a combined material enriched in fiber relative to said starting material. In another particular embodiment, this method further comprises combining said second subfraction with said fourth subfraction, thereby forming a combined material reduced in fiber relative to said starting material.

In an embodiment, the invention provides a method of generating at least one fiber-enriched fraction and at least one fiber-reduced fraction from a processed grain product starting material, comprising: a) separating by size said grain product into a first fraction and a second fraction, wherein said first fraction has a larger particle size and said second fraction has a smaller particle size; and b) a first classifying, wherein said second fraction is classified so as to yield a first subfraction of a lighter material enriched in fiber and a second subfraction of a heavier material reduced in fiber; thereby generating a fiber-enriched fraction and a fiber-reduced fraction from a processed grain product. In an embodiment, this method further comprises combining said first fraction with said first subfraction, thereby forming a combined material enriched in fiber relative to said starting material.

In another embodiment, the method further comprises a step c), a second classifying, wherein said first fraction is classified so as to yield a third subfraction of a lighter material enriched in fiber and a fourth subfraction of a heavier material reduced in fiber. In a particular embodiment, the method further comprises combining said first subfraction with said third subfraction, thereby forming a combined material enriched in fiber relative to said starting material. In another particular embodiment, the method further comprises combining said second subfraction with said fourth subfraction, thereby forming a combined material reduced in fiber relative to said starting material.

The invention provides a method of classifying DDGS, comprising elutriation of DDGS so as to yield a lighter fraction enriched in fiber and a heavier fraction reduced in fiber.

The invention provides a gravity elutriation device for separating fiber from a processed grain product, comprising a vertical flow column, an air inlet connected to said column, a blower operatively connected to said air inlet so as to introduce a fluid flow of air into said column; a feed inlet connected to said column at a point located above said air inlet so as to allow said fluid flow to act as a force on a substance passing from said inlet into said column; a feeder operatively connected to said feed inlet for introducing said processed grain product; and a lighter fraction collection reservoir disposed with respect to said column to receive a portion of said product.

In an embodiment, the elutriation device comprises a heavier fraction or residue collection reservoir proximal to said bottom end, wherein said heavier fraction collection reservoir serves to contain a residual component of said product subjected to said fluid flow.

The invention provides a fiber removal and harvesting apparatus comprising a fluid-flow classifying device, a sieving device, and a conveyor for receiving an output from said classifying device and transporting said output to said sieving device. The invention provides a fiber removal and harvesting apparatus comprising a fluid-flow classifying device, a sieving device, and a conveyor for receiving an output from said sieving device and transporting said output to said classifying device.

The invention provides DDG and DDGS compositions. The invention provides a DDGS composition comprising a fiber content amount. In an embodiment, the fiber content amount is selected from the group consisting of up to about 40%, up to about 35%, up to about 30%, up to about 25%, up to about 20%, up to about 15%, up to about 10%, and up to about 5%. The invention provides a DDGS composition comprising a fiber content amount of about 10% or less. An embodiment of the invention is a DDGS composition comprising a fiber content of from about 5% to about 10%. Embodiments of the invention include a DDGS composition comprising a fiber content percentage selected from the group consisting of about 9%, about 8%, about 7%, about 6%, about 5%, about 4%, about 3%, and about 2%.

An embodiment of the invention is a DDG or DDGS composition enriched in fiber relative to a starting material prepared by methods of the invention. An embodiment of the invention is a DDG or DDGS composition reduced in fiber relative to a starting material prepared by methods of the invention.

The invention provides a feed product or feed product supplement digestible by non-ruminant animals. In a particular embodiment, the feed product or feed product supplement comprises processed DDGS wherein said DDGS has a fiber content selected from the group consisting of about 10% or less, about 8% or less, and about 6% or less.

The invention provides a method of modifying ethanol production so as to integrate a DDG or DDGS fiber removal process comprising the steps of: a) classifying said DDG or DDGS so as to yield a lighter fraction and a heavier fraction; b) sieving said DDG or DDGS so as to yield a larger particle size fraction and a smaller particle size fraction; c. characterizing at least one said lighter fraction, heavier fraction, larger fraction, and smaller fraction regarding fiber content; and d) removing at least one of said lighter fraction, heavier fraction, larger fraction, and smaller fraction characterized as having enriched fiber content relative to a starting material; thereby modifying ethanol production so as to integrate a DDG or DDGS fiber removal process.

The invention provides a method of processing a DDG or DDGS starting material, comprising; a. determining whether a first processing step should be a procedure of classifying or separating by size; and a second processing step should be the procedure not chosen for the first processing step; and b. selecting at least one classification parameter or at least one sieving parameter depending on said determining step. In an embodiment, at least one classification parameter is selected from the group consisting of air velocity rate, treatment time, a physical property of an average starting material, and a physical property of a specific batch of starting material. In an embodiment, a sieving parameter is selected from the group consisting of a pore size, agitation frequency, sieve capacity, treatment time, a physical property of an average starting material, and a physical property of a specific batch of starting material. In an embodiment, the method further comprises one or more further separation steps, wherein a step can be classifying or sieving.

In an embodiment, one or more steps follow an initial combination of sieving and classification (e.g. elutriation). For example, an entire process can comprise sieving, classifying, and sieving; another entire process comprises sieving, classifying, sieving, and classifying; and so forth. Optionally the order of steps in embodiments of the invention is such that classifying (e.g. elutriation) precedes sieving.

In an embodiment, classifying employs an air classification system. In a particular embodiment, the air classification system is selected from the group consisting of: static cyclone, cyclone classifiers, single or multi-stage dynamic classifiers, cross-flow classifiers, spiral separators, high energy dispersion classifiers, and turbine classifiers (single and multiple wheel). In an embodiment, an air classification system can employ a packed bed, fluidized bed, spouted bed, or other approach to facilitate or enhance particle manipulation. In an embodiment, an air classification system can incorporate features of a uniform aerodynamic deduster that has been described for use in dust particle separation (See such described by Yuanhui Zhang of the University of Illinois; e.g. Zhang et al., 1998).

An embodiment of the invention is a fiber-enriched composition wherein said composition comprises a fiber content selected from the group consisting of about 10% or more, about 20% or more, about 30% or more, about 40% or more, about 50% or more, and about 60% or more.

An embodiment of the invention is a residual fraction composition wherein said composition comprises a crude protein content selected from the group consisting of about 50% or less, about 40% or less, about 30% or less, about 20% or less, and about 10% or less.

An embodiment of the invention is a residual fraction composition wherein said composition comprises a crude fat content selected from the group consisting of about 40% or less, about 30% or less, about 20% or less, and about 10% or less.

In an embodiment, a fiber-enriched fraction or composition generated from, DDGS or DDG comprises corn fiber gum or corn fiber oil. In a particular embodiment, a fiber-enriched fraction or composition comprises phytosterols. In a preferred embodiment, the phytosterols are present in a pharmaceutically effective or nutraceutically effective amount.

The invention provides methods, devices, and compositions relating to the removal of fiber from DDGS products.

Embodiments of the invention are applicable to DDGS products of the ethanol industry, for example, the DDGS product of the conventional dry grind ethanol process and the modified DDGS product of the modified dry grind ethanol process such as described by Singh et al., 2001.

In preferred embodiments of the invention, processed DDG or DDGS maintains the bright golden yellow color often associated with a DDG or DDGS product regarded as being of high quality.

In an embodiment, a process, device, or composition is readily adaptable to a modern ethanol production plant. For example, a process or device of the invention can be added as a module to a current end point in a plant without substantially interfering with an upstream item or activity.

DETAILED DESCRIPTION OF THE INVENTION

The invention may be further understood by the following non-limiting examples.

Example 1

Method of Removing Fiber from DDGS

Figure 4:
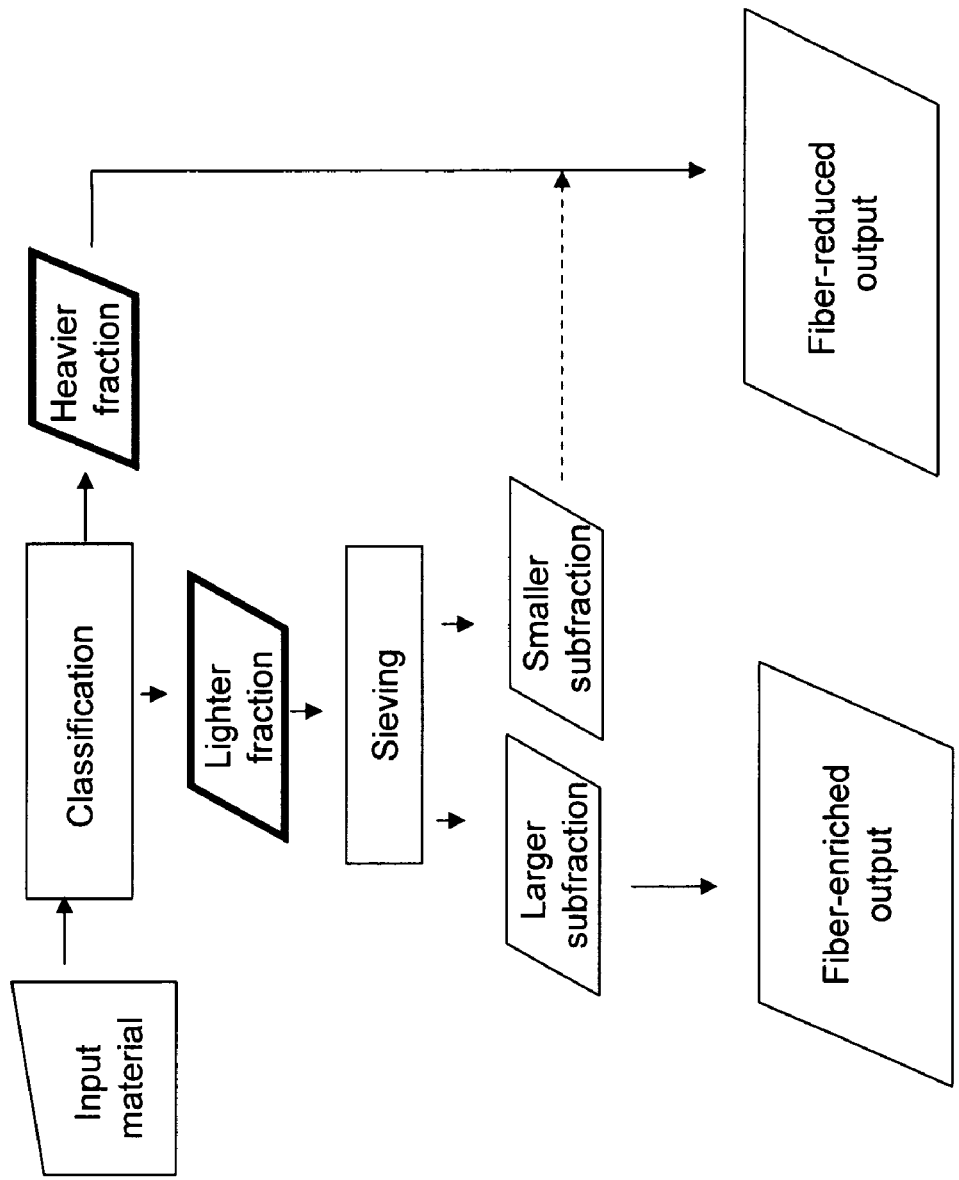
FIG. 4. Flowchart of fiber removal process with elutriation then sieving.

FIG. 4 illustrates a flow chart of a fiber removal process. Input material is first subjected to classification, such as by gravity air elutriation. This separates the input material into heavier and lighter fractions. The lighter fraction is then sieved into a larger subfraction and a smaller subfraction. The initial heavier fraction can be combined with the smaller subfraction from sieving to yield a fiber-reduced output. The larger subfraction from sieving yields a fiber-enriched output.

Figure 1A:
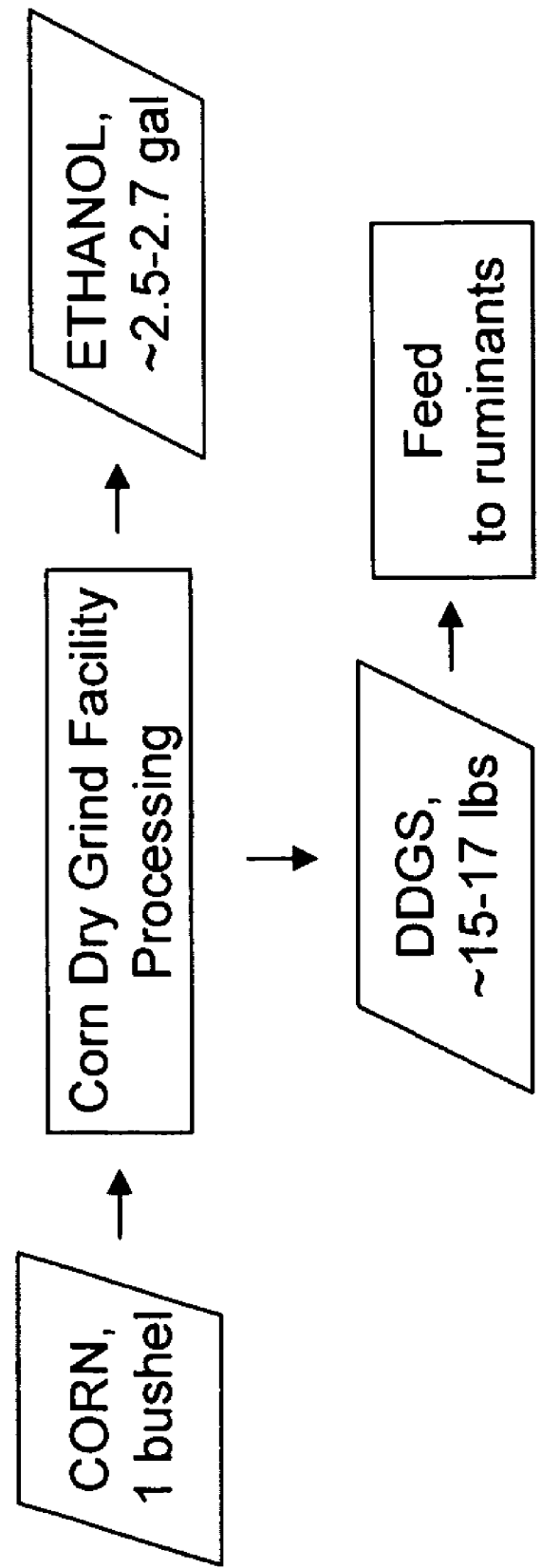
FIGS. 1A and 1B. Overview and schematic of the conventional dry grind ethanol process.
Figure 1B:
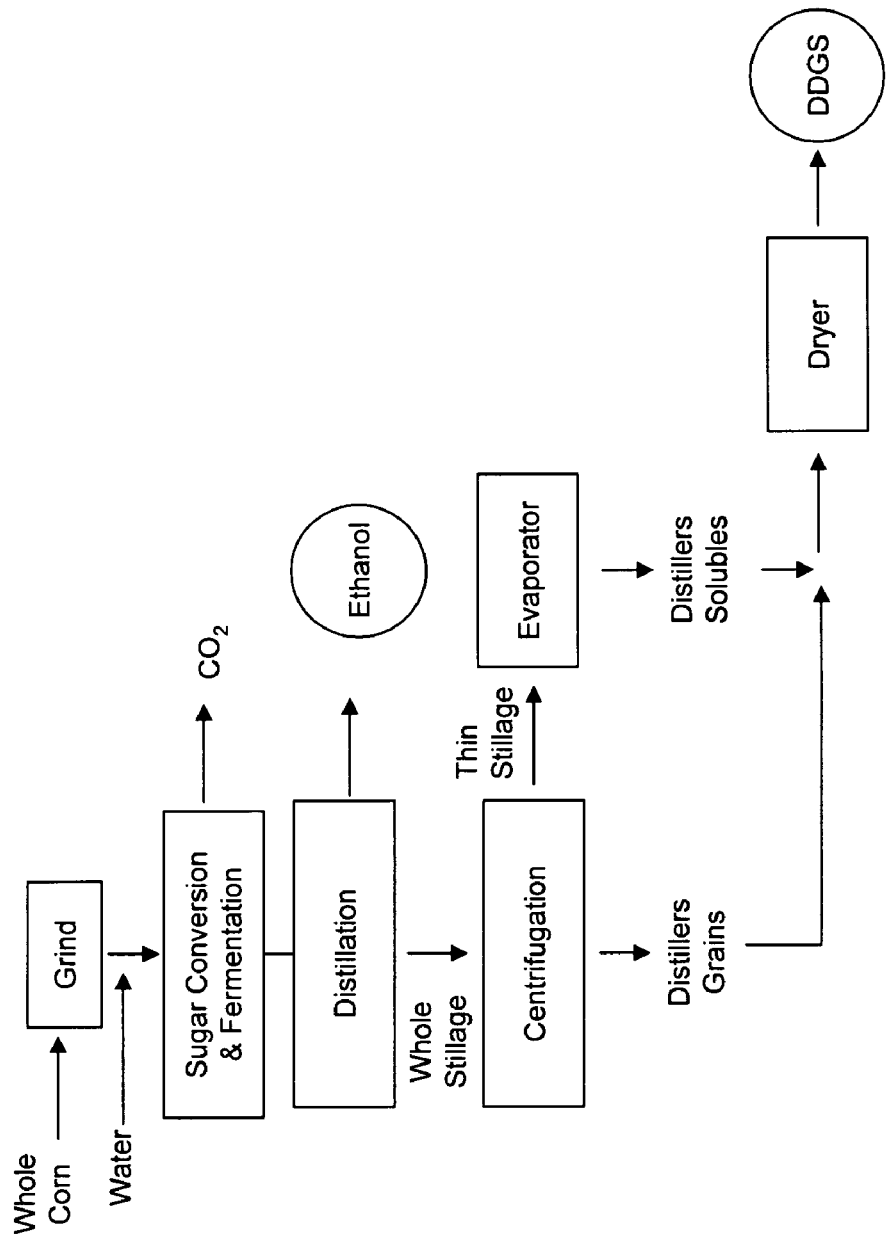
Figure 2:
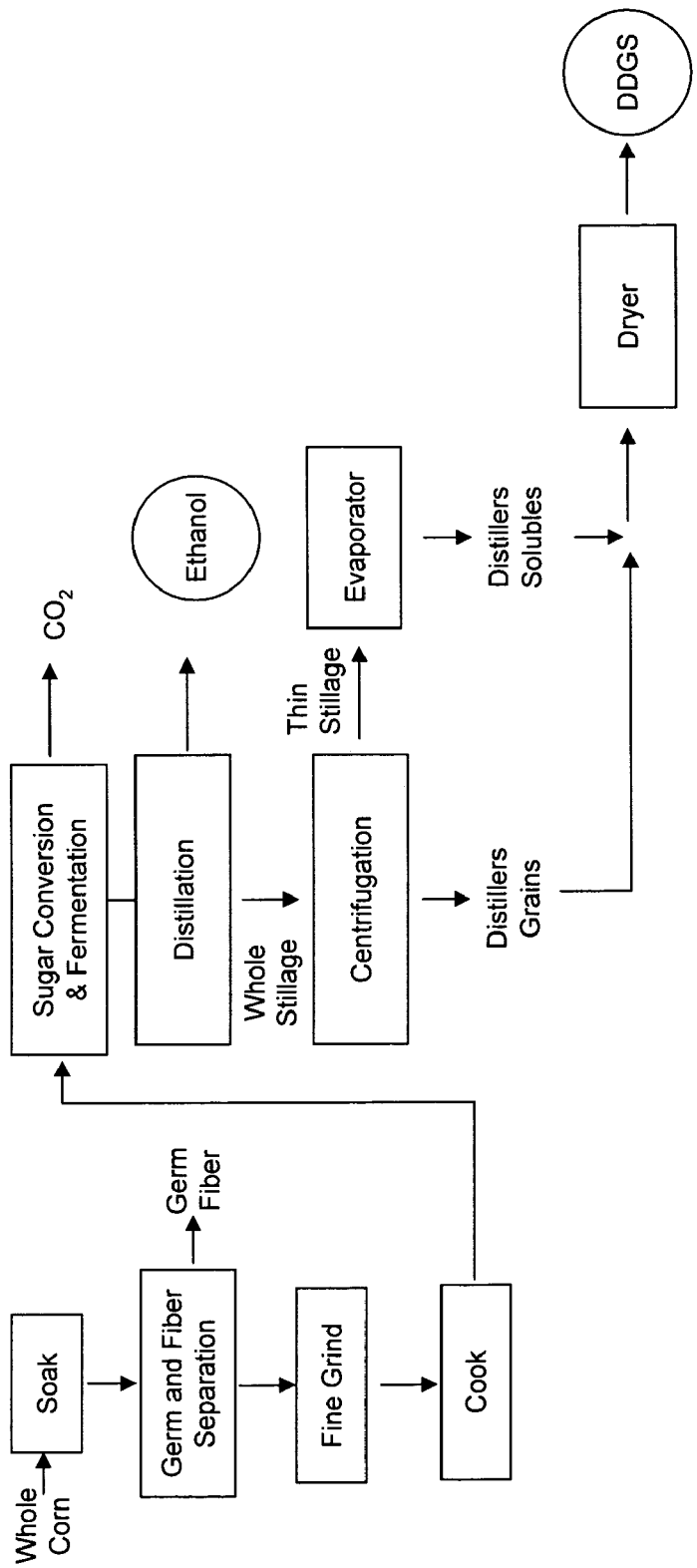
FIG. 2. Schematic of the modified dry grind ethanol process.
Figure 3:
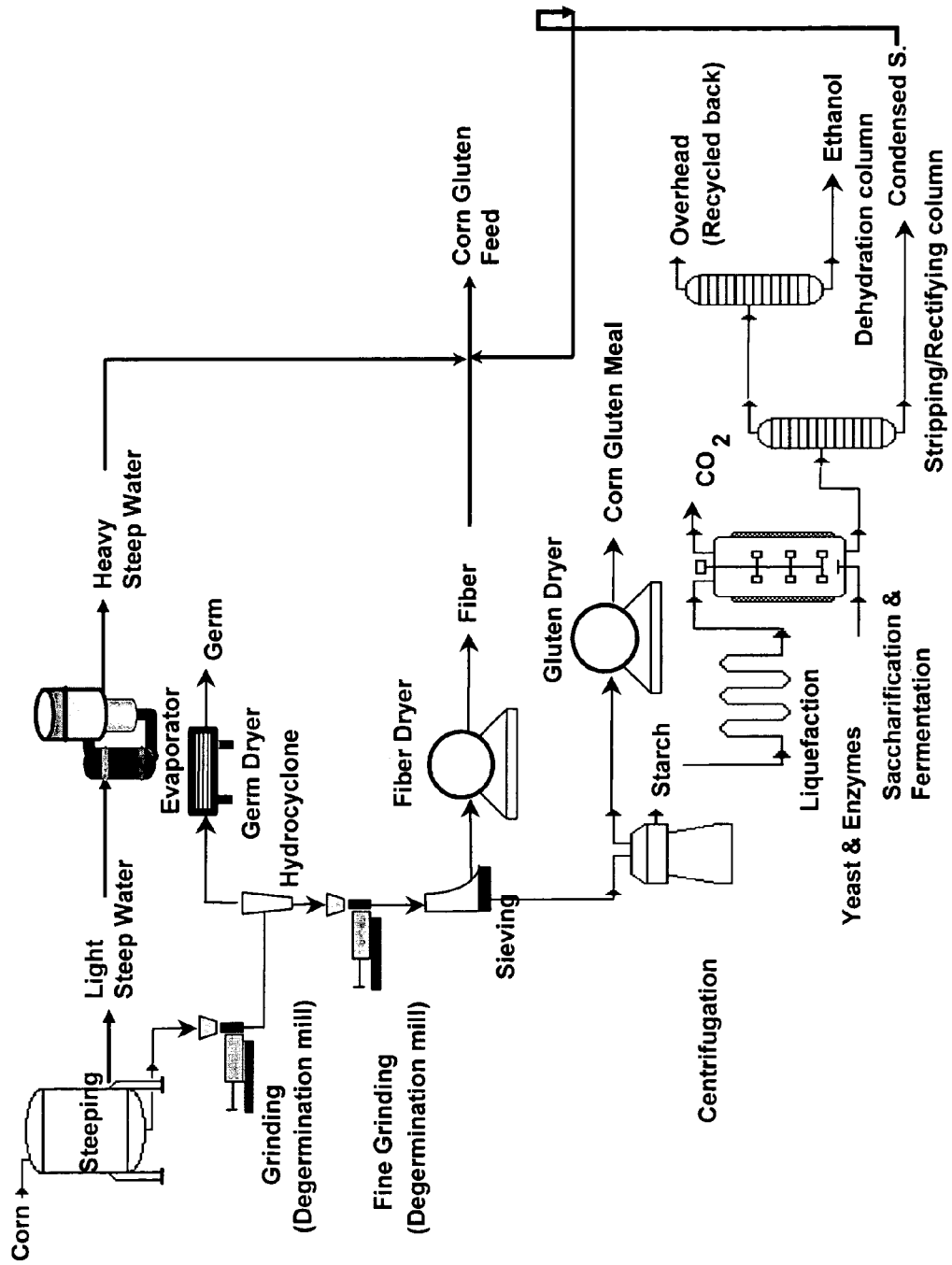
FIG. 3. Schematic of the corn wet milling process.

In a particular example, the input material is DDGS. DDGS is conventionally produced in an ethanol processing plant using the Dry Grind process. See FIG. 1. In an embodiment of the invention, the fiber content of conventionally produced DDGS is reduced to yield an enhanced DDGS. This enhanced DDGS can be used as feed product for non-ruminant agricultural animals, such as swine and poultry, in addition to still being suitable for ruminants. Additionally, enhanced DDGS can be used as a feed or supplement for non-agricultural animals including companion animals such as dogs and cats. Furthermore, enhanced DDGS can also be used as a human food, for example in gourmet human cuisine.

During elutriation, an initial DDGS batch is exposed to the fluid flow force of an air stream. The force acts to separate or differentiate the DDGS into a heavier fraction and a lighter fraction. The heavier fraction is reduced in fiber content. The heavier fraction can also be referred to as "DDGS residue." The lighter fraction is enriched in fiber content.

It has surprisingly been found that some particles of non-fiber components, however, are carried along by the air force despite their relatively greater density; these tend to be smaller particles with a correspondingly lighter absolute weight. The lighter fraction is thus significantly enriched in fiber but also comprises non-fiber particle components of the original DDGS starting material. Without wishing to be bound by a particular theory, it is believed that an explanation for the makeup of the elutriated lighter fraction is as follows. As the original DDGS is subjected to forces in elutriation, the forces experienced by large-sized light particles and small-sized denser particles are the same. The air force may discriminate on the basis of a combination of factors such as particle mass, weight, volume, density, and shape. Generally, many particles of the fiber component of DDGS are larger in size and lighter in weight than particles of non-fiber components of DDGS.

After elutriation, one or more characteristics of fiber and non-fiber particles are exploited by size separation, such as by screening or sieving, to obtain further products. The further products include an enriched, cleaner or purer fiber product and a fiber-reduced product. Screening the lighter fraction material that comes out with the air therefore allows separate recovery of fiber and non-fiber material. The combination of elutriation and sieving is found to be effective in generating reduced-fiber DDGS and a fiber-enriched product from DDGS starting material.

During sieving, the larger particles that do not pass through the sieve are enriched or relatively pure fiber. Smaller particles that are sieved are reduced in fiber and enriched in protein and/or fat content. Sieving the elutriated lighter fraction thus yields a larger particle size subfraction and a smaller particle size subfraction. The sieved smaller particle size subfraction can be added to the DDGS residue. The combination of the sieved smaller subfraction and the DDGS residue can be referred to as "enhanced DDGS." Alternatively, DDGS residue alone can be referred to as "enhanced DDGS."

The DDGS residue can optionally be sieved before or after being combined with the sieved smaller particle size subfraction.

The elutriated lighter fraction can be used as a source of enriched fiber. Following sieving of this lighter fraction, the larger particle size subfraction can be used as a source of fiber that is yet further enriched in its fiber proportion relative to starting material.

Figure 9:
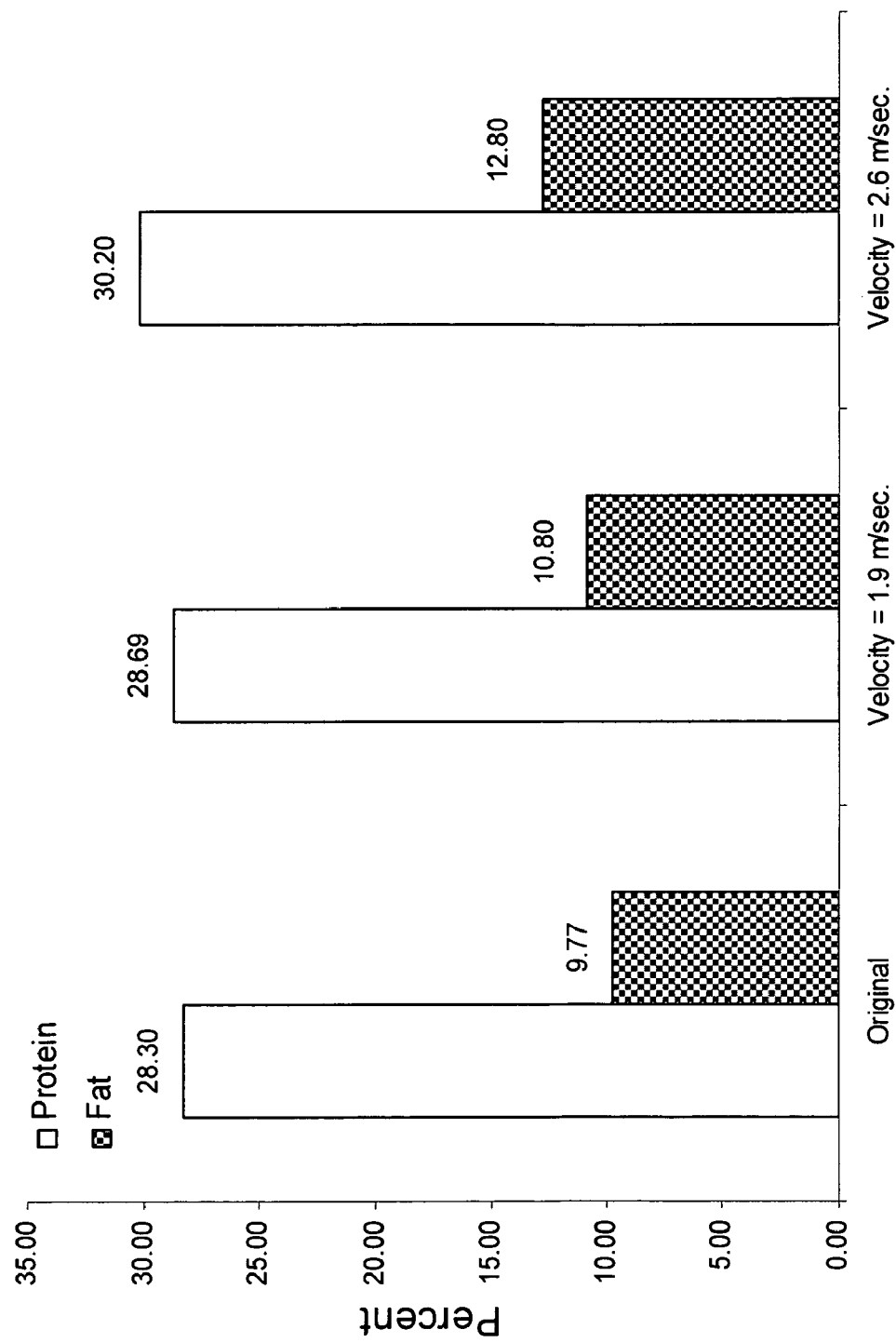
FIG. 9. Graph illustrating protein and fat content data in heavy fractions harvested from processing DDGS by elutriation at different air flow rates.

In a specific example, original DDGS material was subjected to gravity air elutriation. The air velocity was 1.9 m/s (meters per second) or 2.6 m/s. The protein and fat content from heavy fractions were analyzed. See FIG. 9. The original DDGS material had an initial protein content of 28.30% and fat content of 9.77%. Under the condition of air velocity at 1.9 m/s, the recovered heavy fraction had a protein content of 28.69% and a fat content of 10.80%. Under the condition of air velocity at a rate of 2.6 m/sec, the recovered heavy fraction had a protein content of 30.20% and a fat content of 12.80%. The increase in air velocity thus contributed to an increased percentage of both protein and fat in the recovered heavy fraction. Calculations of protein and fat content were performed based on a percentage of dry matter.

Figure 10:
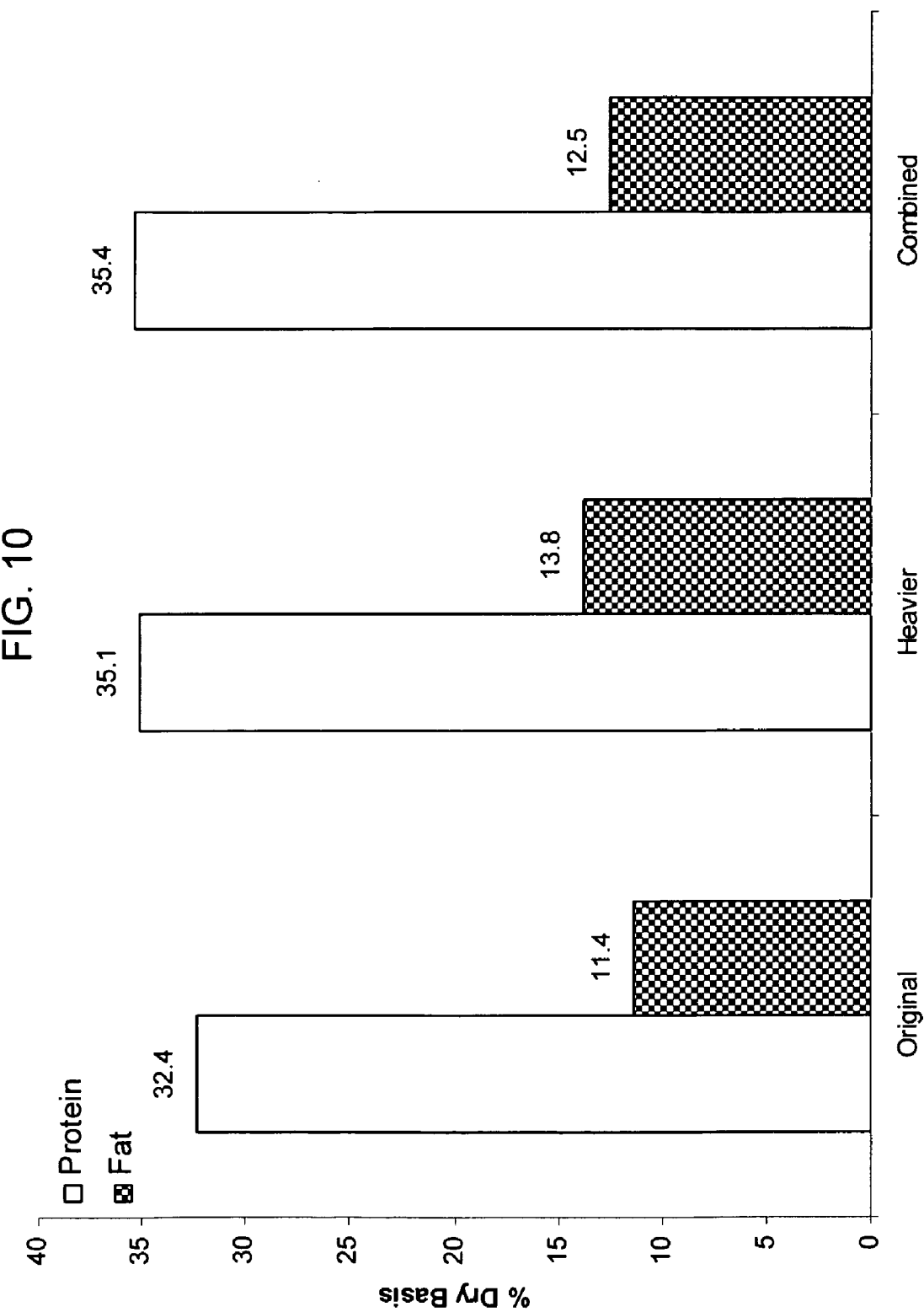
FIG. 10. Graph of protein and fat content data of DDGS outputs after elutriation at an air velocity of 2.6 meters per second.

For data In FIG. 10, original DDGS material was processed by elutriation then sieving. First, gravity air elutriation was performed at an air velocity rate of 2.6 m/s, separating DDGS into lighter and heavier fractions. Next, the lighter fraction was sieved to generate a larger particle size subfraction and a smaller particle size subfraction. A sample of the heavier fraction was analyzed. Material referred to as "combined" here was prepared by combining the heavier fraction with the smaller particle size subfraction from sieving. Samples from both the heavier and combined material demonstrated increases in protein and fat content on a percentage of dry matter basis relative to the original DDGS material. The heavier or combined DDGS material is therefore enriched in protein and fat content.

Figure 11:
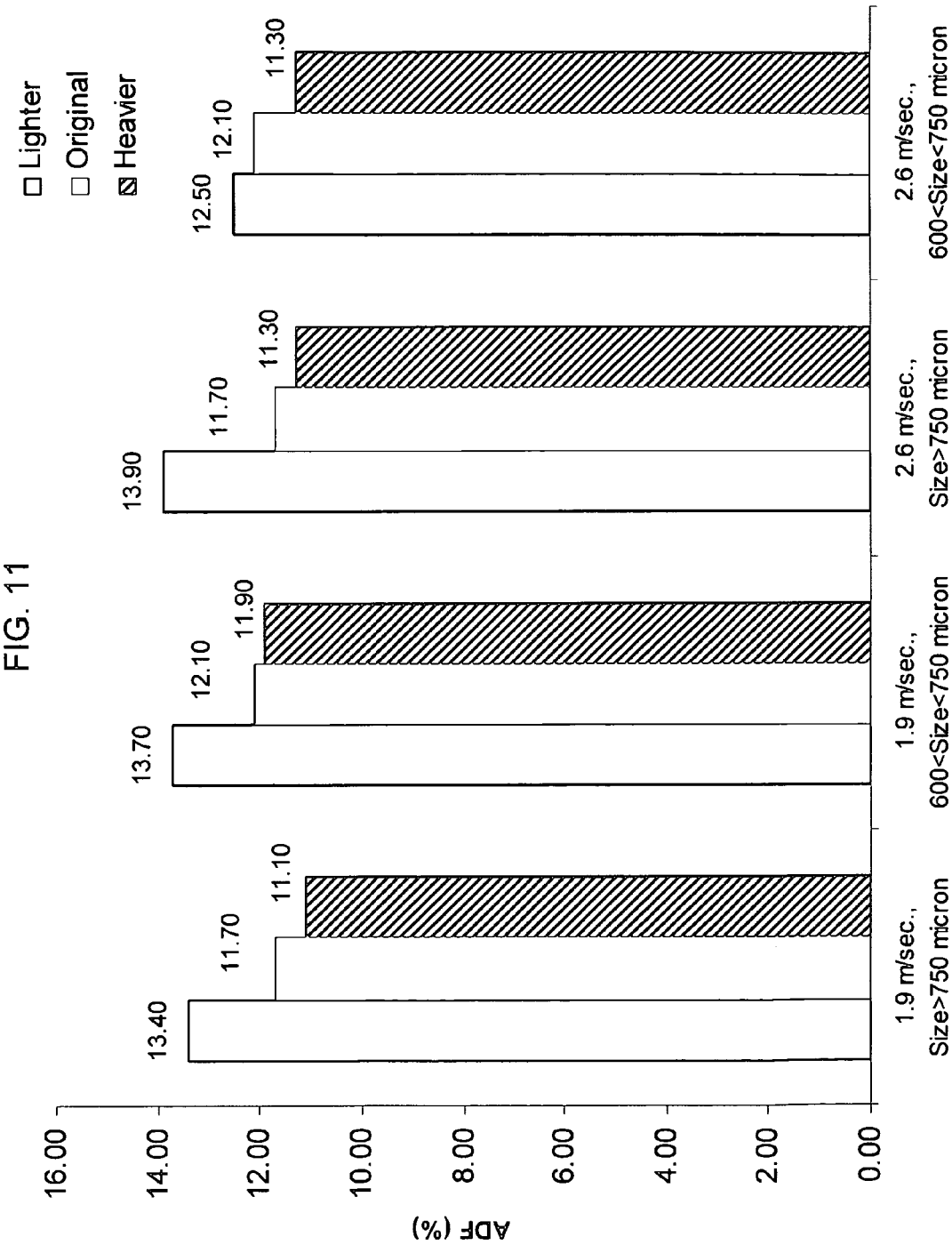
FIG. 11. Graph illustrating acid detergent fiber (ADF) percentage data from processed DDGS products of original, lighter, and heavier fractions resulting from elutriation at various air flow rates followed by sieving of various particle size ranges relative to a size X: (a) X>750 micron at 1.9 m/sec; (b) 600<X<750 micron at 1.9 m/sec; (c) X>750 micron at 2.6 m/sec; and (d) 600<X<750 micron at 2.6 m/sec.

The combination of elutriation and sieving was effective in generating from original DDGS material a fiber-enriched lighter fraction and a fiber-reduced heavier fraction. FIG. 11 indicates data from acid detergent fiber measurements (ADF %) of DDGS material processed under certain combinations of conditions. Elutriation was performed at air velocity rates of 1.9 or 2.6 m/s to generate lighter and heavier fractions from DDGS original material. Sieving was performed using pore sizes of 600 microns and 750 microns. Relative to original material, lighter fraction material was consistently found to be higher or enriched in fiber content, and heavier fraction material was consistently found to be lower or reduced in fiber content. At the same flow rate, lighter fraction material not passing through a sieve opening of 750 microns consistently had a fiber content greater than material with a particle size of between 600 and 750 microns. Sieving was performed using pore sizes of 600 microns, 750 microns, or 850 microns.

Figure 12:
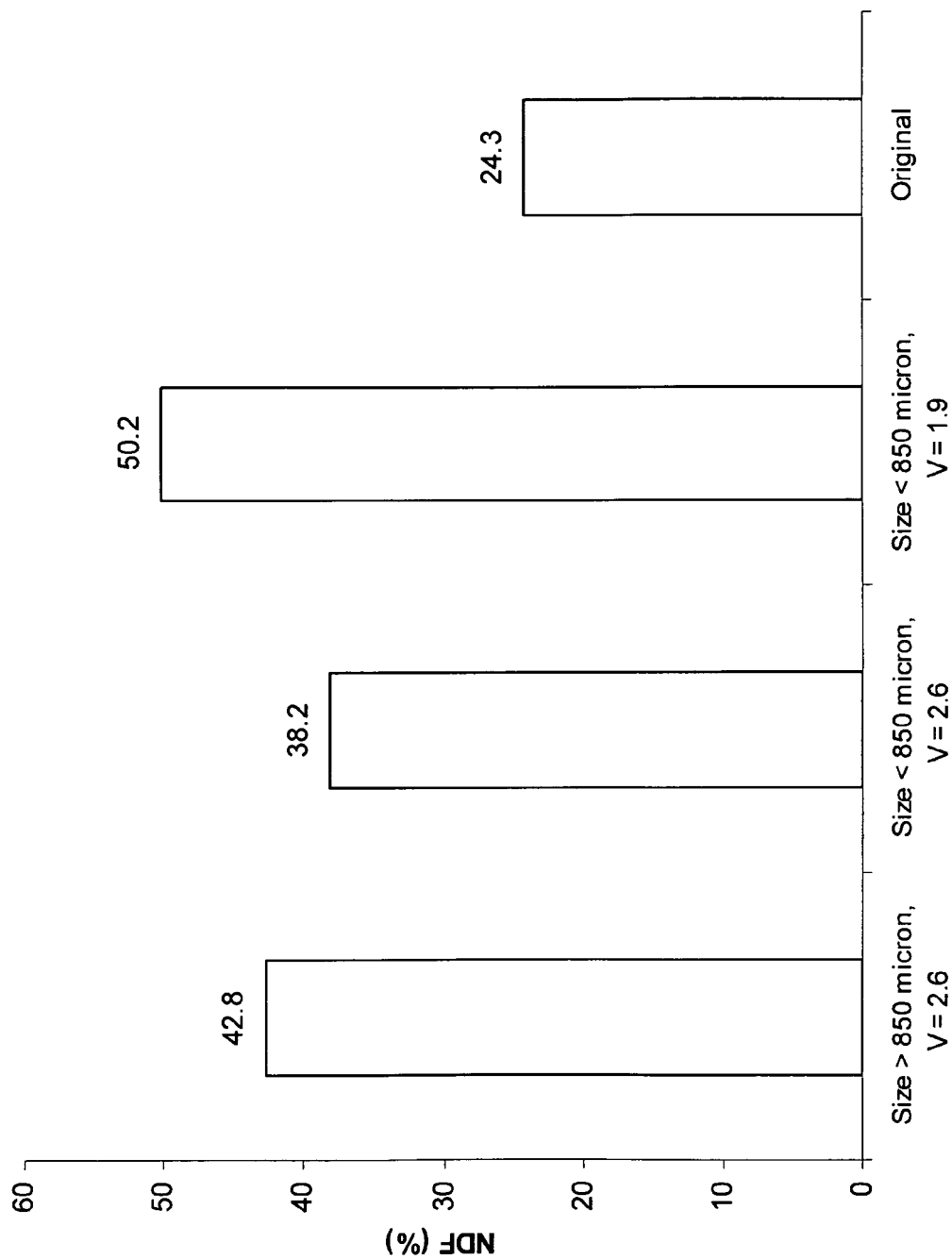
FIG. 12. Graph illustrating neutral detergent fiber (NDF) percentage data from processed DDGS products of original and lighter fractions of various particle size ranges.

An experiment was performed to assess optimal velocity conditions for fiber enrichment of lighter fractions. FIG. 12 shows results of neutral detergent fiber percentage measurements for processed DDGS samples. Elutriation was performed at air velocity rates of 1.9 or 2.6 m/s and lighter fractions were collected. Next, sieving was performed with an opening size of 850 microns. A lower flow rate resulted in a lighter fraction with a significantly enriched fiber content of more than double that of the original starting material. At the elevated flow rate of 2.6 m/s, an enhancement of fiber content was also observed but not as great as at the lower air velocity. Larger sieved particles (>850 micron) of the lighter fraction obtained at 2.6 m/s had greater fiber content than smaller sieved particles (<850 micron).

Example 2

Elutriation Apparatus

Figure 6:
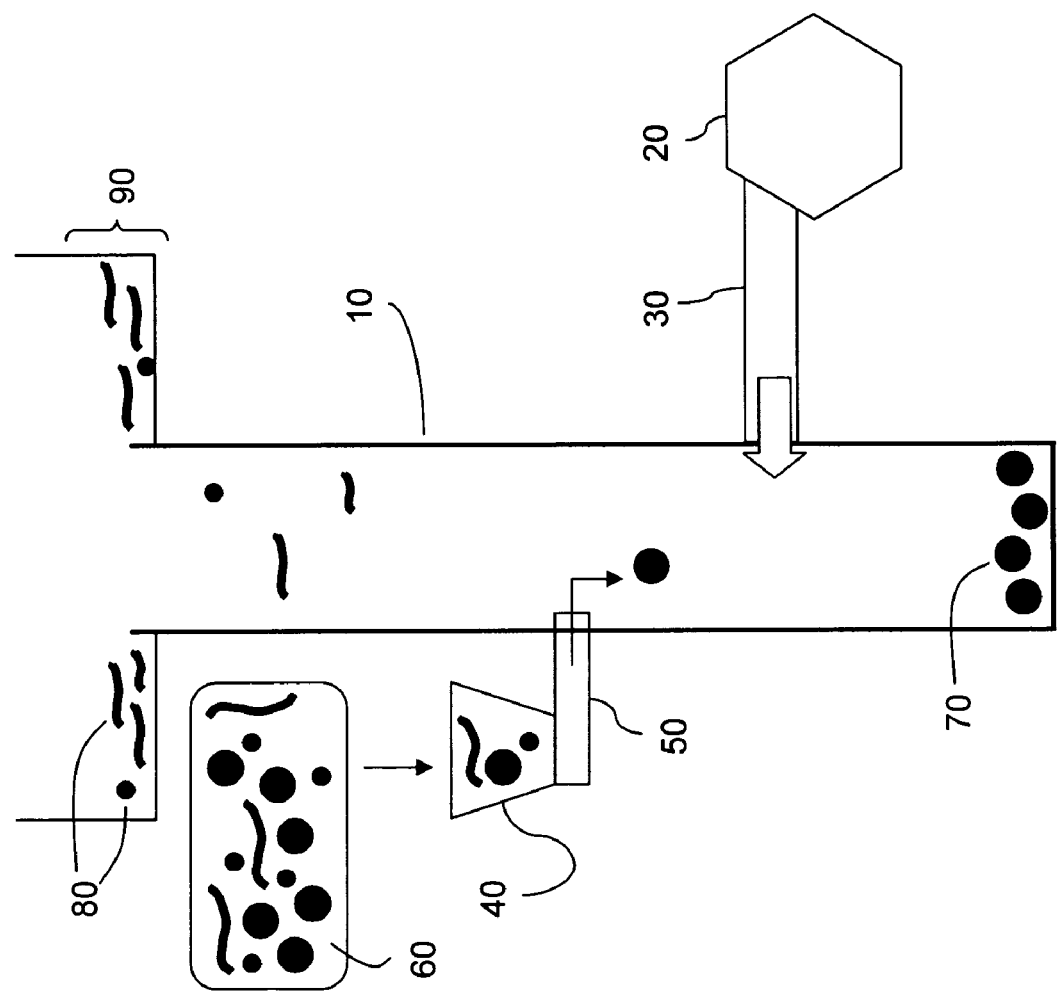
FIG. 6. Schematic of elutriation apparatus.
Figure 7:
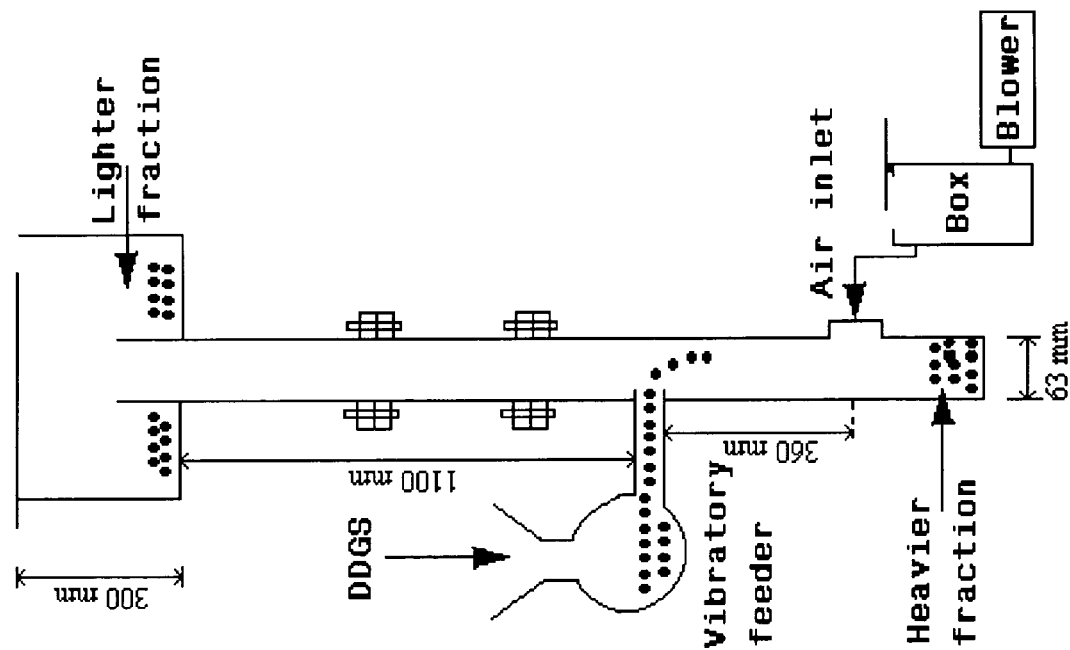
FIG. 7. Schematic of a specific embodiment of an elutriation apparatus used for DDGS.
Figure 8:
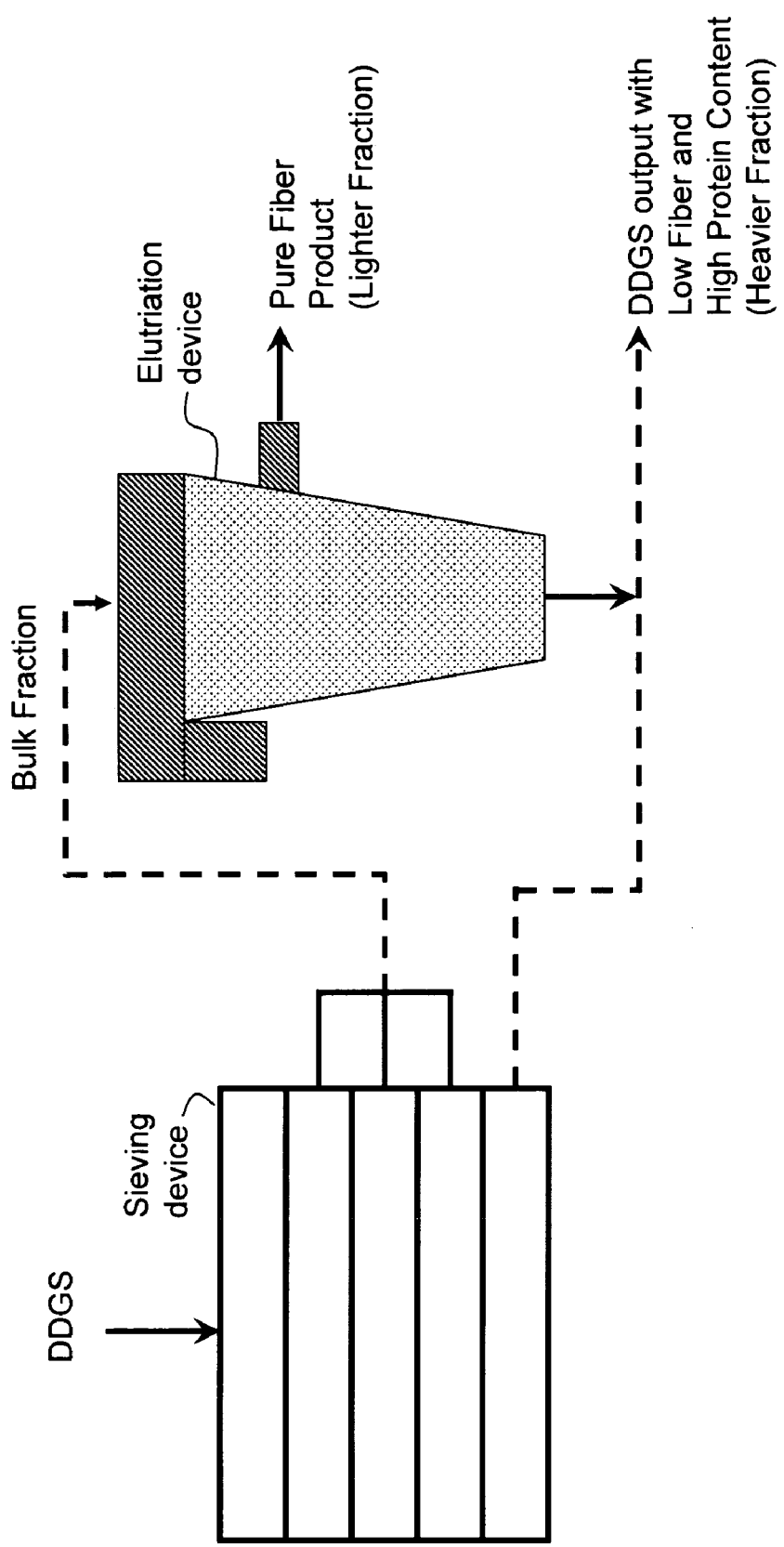
FIG. 8. Schematic of a specific embodiment of a method of processing DDGS.

See FIG. 6. An elutriation column 10 is connected to a fan or air blower 20 via an air inlet 30. A feeder 40 is connected to column 10 via a feeder inlet 50. Input material 60, comprised of light components and heavy components, is introduced to column 10 using feeder 40. Output residue or heavier fraction 70 collects at the bottom end of column 10. Output lighter fraction 80 is carried by fluid flow to one or more collection reservoirs 90. See also FIG. 7.

A feeder is used as known in the art. For example, the feeder can be a vibratory feeder, auger, hopper, conveyer, or dumper container optionally mechanized. Used in several examples herein, a preferred vibratory feeder is POWDERTEC 3090 Sample Mill. A blower used in several examples herein is Dayton Model No. 2C701.

The elutriation column used in certain examples herein has a height of 61 inches above the feeding inlet and a diameter of 2.5 inches.

Example 3

Sieving Apparatus

A sieving apparatus is used as known in the art. In several examples herein, the separator used was a Sweco Vibro-Energy Separator, Model No. LS18S883.

Example 4

Elutriation in a Horizontal Flow Column

In an embodiment, the elutriation is performed using a horizontal flow column. The input material such as DDGS is introduced in a first direction of flow and is acted upon by an airstream force at an angle such as orthogonal to the first direction.

Example 5

Enhanced DDGS from Elutriation Only

Enhanced DDGS is produced in the form of DDGS residue using the elutriation process as described herein. In this example, it is not necessary to add to the DDGS residue the smaller particle size subfraction resulting from a sieving step.

Example 6

Use of DDG as Input Material

Embodiments of the invention are also applicable when DDG is used as the input material. Enhanced DDG is produced in the form of DDG residue using the elutriation process as described herein. Sieving can be used to further separate the DDG lighter fraction into a larger particle size subfraction and smaller particle size subfraction. In another embodiment, it is not necessary to add to the DDG residue the smaller particle size subfraction resulting from a sieving step. Input DDG material is also used in the generation of relatively pure fiber from the combination of elutriation and sieving, where relatively pure fiber is recovered from the sieved larger particle size subfraction of the elutriated lighter fraction.

Example 7

Fiber Removal Process Where Sieving Precedes Elutriation

Summary—sieving followed by elutriation to remove fiber from DDGS

Objective: To determine the dependence of composition of heavier and lighter fractions on the velocity of air in the elutriation column for each screen size category.

Results: 1) Sieving alone produces two size categories (B60 and BPan) that contain low fiber content (36.1% reduction in NDF for BPan) and are enriched in protein/fat (26.7% enhancement in protein for BPan). These two fractions comprise about 40% of the mass of the original DDGS. 2) There is excellent removal of fiber from the DDGS by air elutriation. NDF (Neutral Detergent Fiber) values obtained for the lighter fraction are as high as 58.7%. The velocity ranges used for experimentation in the size categories are as follows: B20—2.23 to 4.08 m/sec., B30—1.84 to 2.83 m/sec. and B40—1.80 to 2.32 m/sec. The fiber fraction can be used to make valuable products, such as, phytosterols, corn fiber gum and corn fiber oil. 3) The enhancement in protein content in the heavier fractions in comparison to the bulk of the size category is as high as 28.13%. 4) The enhancement in fat content in the heavier fractions in comparison to the bulk of the size category is as high as 65.79%. 5) The reduction in NDF in the heavier fractions in comparison to the bulk is as high as 36.03%. 6) The enhancement in Total Digestible Nutrients (TDN) in the heavier fractions in comparison to the bulk is as high as 6.15%.

Application: Thus sieving followed by elutriation can be used to separate DDGS into a fiber enriched fraction and many residual fractions with enhanced protein/fat content and reduced fiber content. These residual fractions can be used or mixed in appropriate combinations so as to extract an optimal or maximum revenue from the high-value residuals. The residuals with less fiber content can now be used as feed product for non-ruminant animals and the fiber can be used to make other valuable products.

Experiments were conducted on commercial sample of DDGS obtained from a commercial dry grind ethanol plant. The average particle size was about 565 microns. Sieving was done using a SWECO Vibro-Energy separator with mesh sizes as follows.

TABLE 1

Sieves used and weight percent of material retained on each screen.

| Mesh Category | Opening in microns | Referred to as | Wt. % |
|---|---|---|---|
| 24T | 870 | B20 | 26.99 |
| 34T | 580 | B30 | 19.45 |
| 35M | 425 | B40 | 13.29 |
| 60M | 235 | B60 | 20.11 |
| Pan | 0 | BPan | 20.16 |

Figure 13:
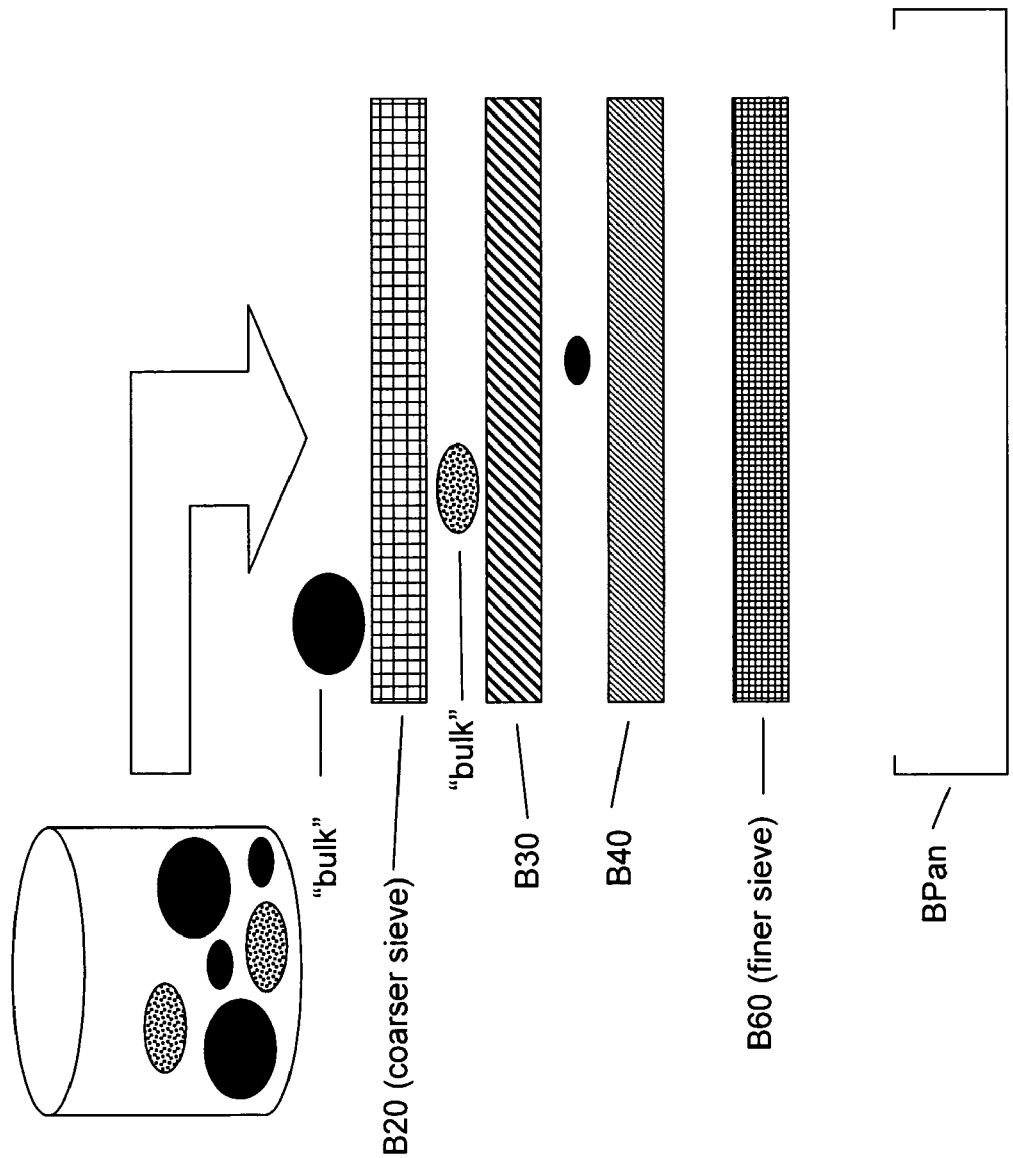
FIG. 13. Schematic of tiered sieving screens.
Figure 14:
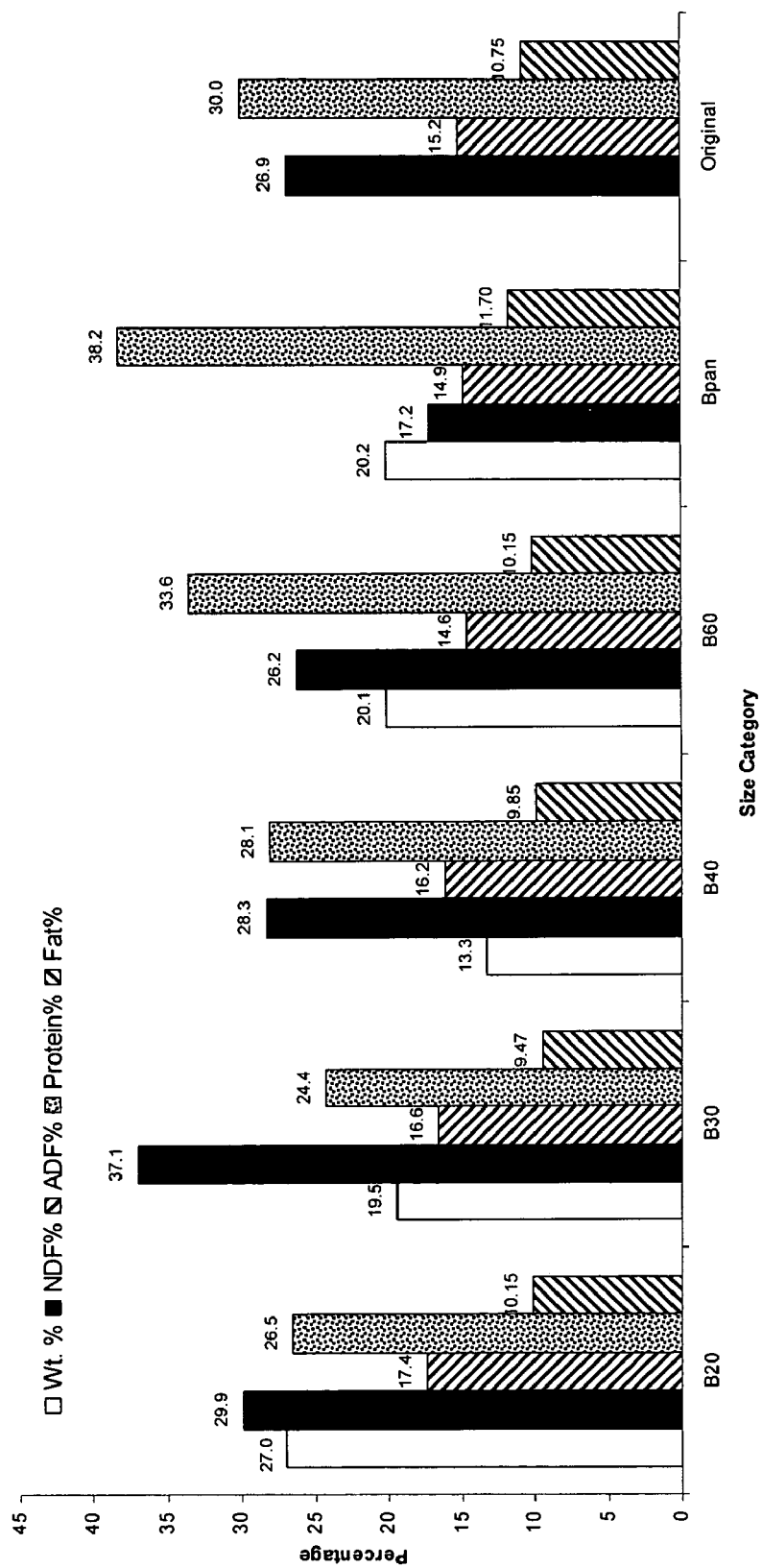
FIG. 14. Graph of input weight distribution and composition of materials (neutral detergent fiber, acid detergent fiber, protein, and fat) after sieving using various screen sizes (i.e., composition of size categories).
Figure 15:
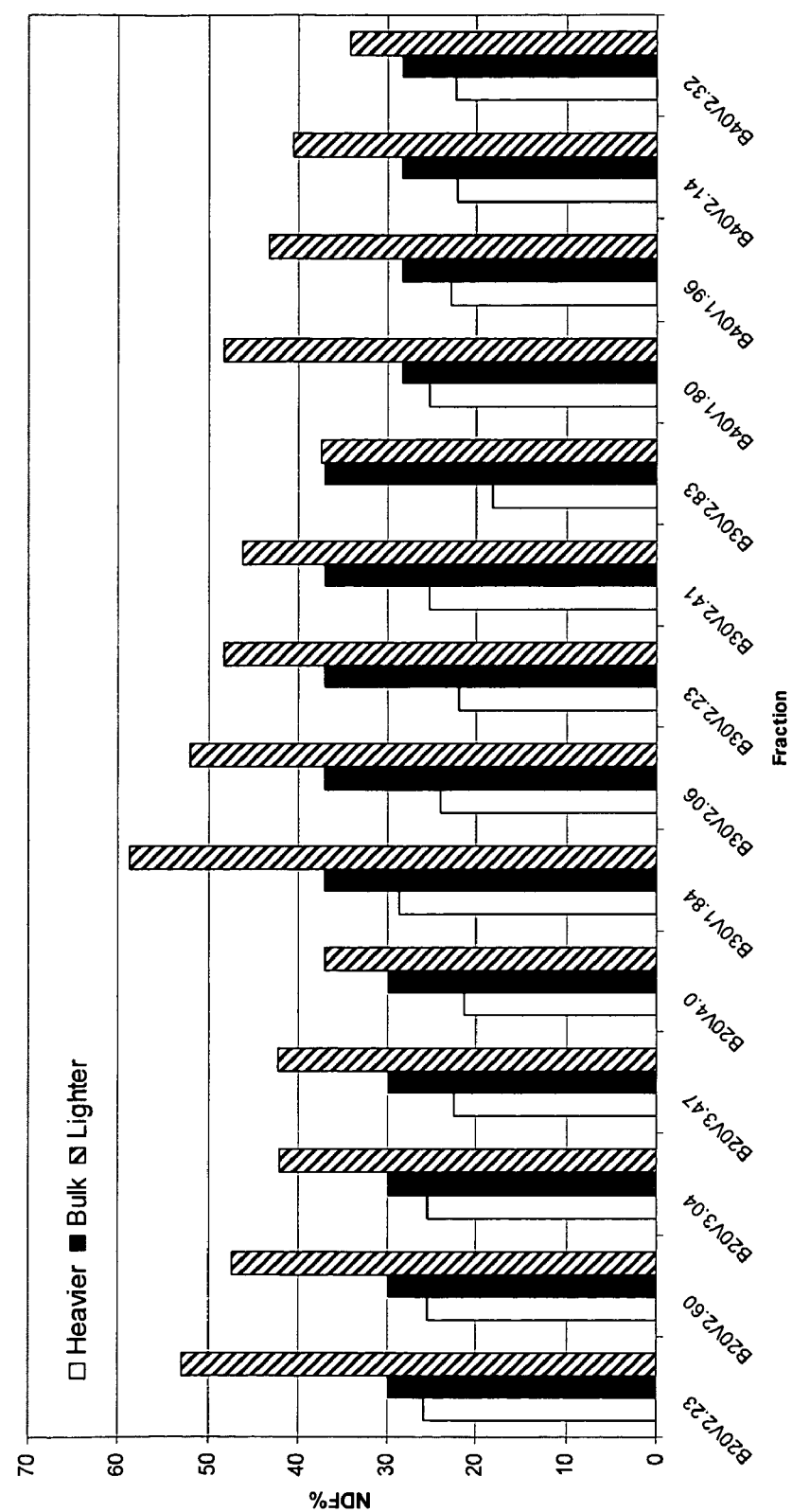
FIG. 15. Graph of neutral detergent fiber (NDF) percentage data for heavier, bulk, and lighter fractions generated from a process of sieving with various screen sizes (e.g., B20, B30, B40) followed by elutriation at various air velocity rates (e.g. V2.23=velocity of 2.23 m/sec, etc.).
Figure 16:
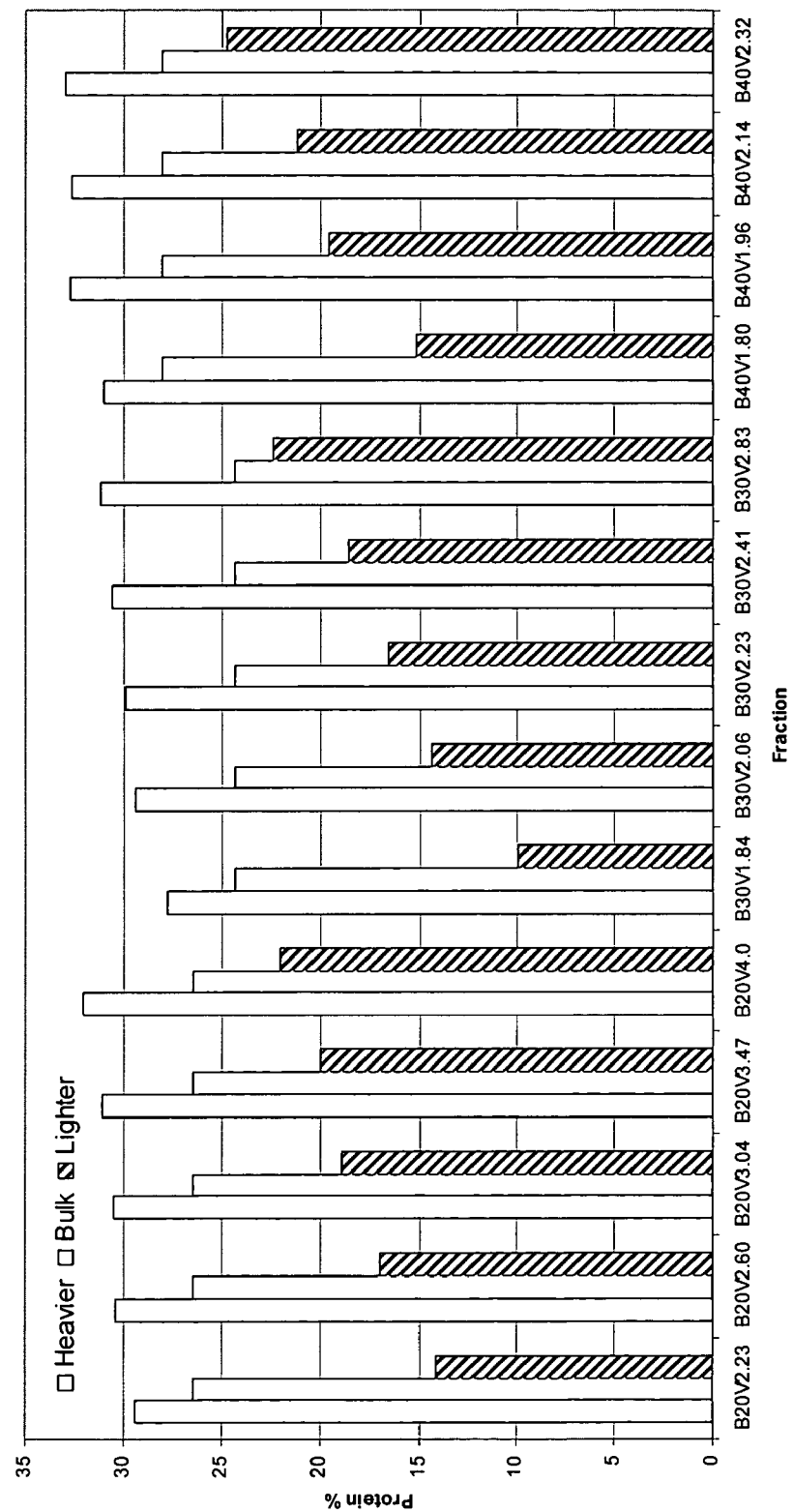
FIG. 16. Graph of protein data for heavier, bulk, and lighter fractions generated from a process of sieving with various screen sizes followed by elutriation at various air velocity rates.
Figure 17:
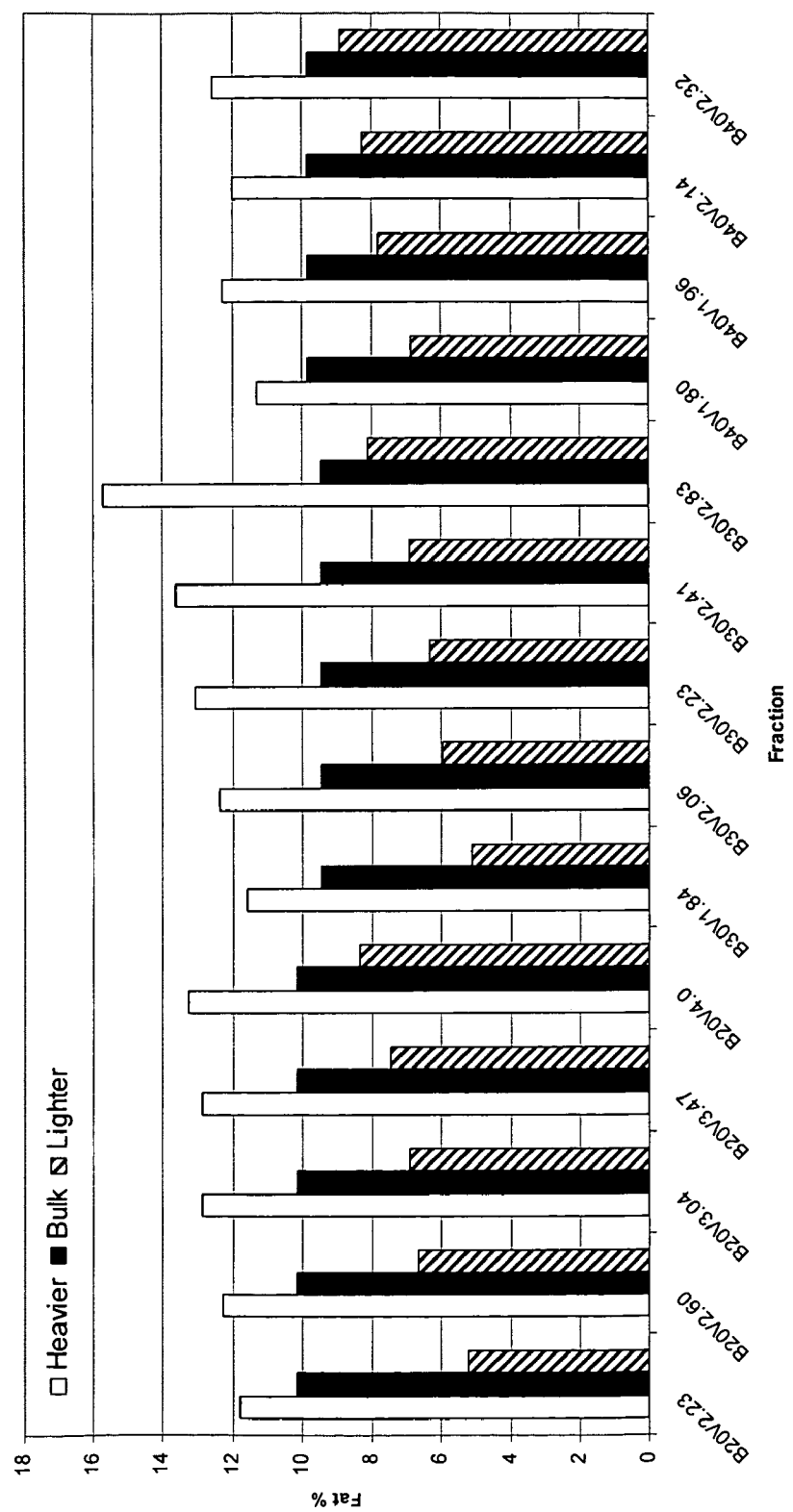
FIG. 17. Graph of fat data for heavier, bulk, and lighter fractions generated from a process of sieving with various screen sizes followed by elutriation at various air velocity rates.
Figure 18:
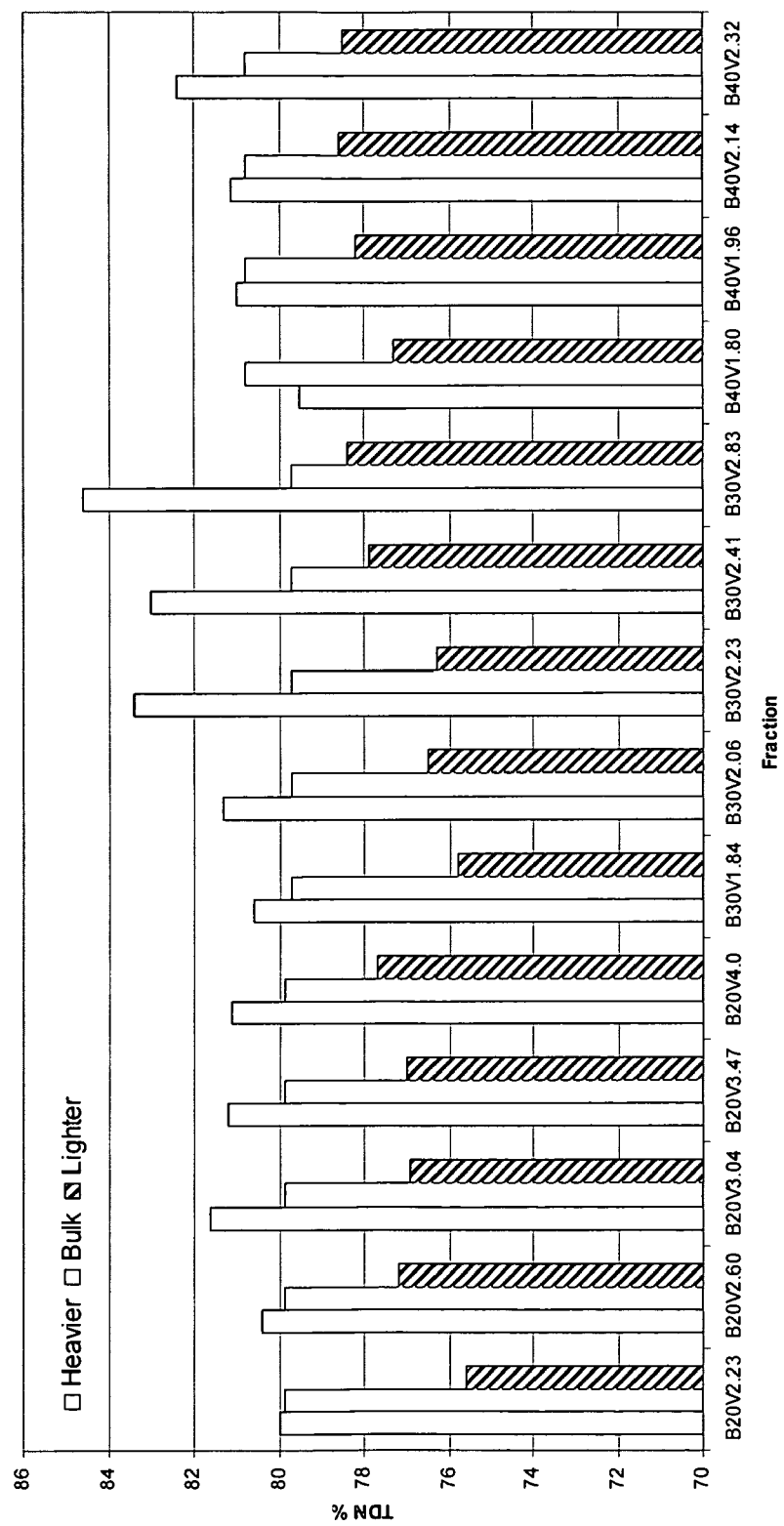
FIG. 18. Graph of total digestible nutrients for heavier, bulk, and lighter fractions generated from a process of sieving with various screen sizes followed by elutriation at various air velocity rates.

The Bulk (B) refers to material on the top of each screen, i.e. the material not passing through a given screen. Screens are arranged relatively as illustrated in FIG. 13. The bulk and each size category were analyzed for composition and the results were tabulated; see Table 2.

TABLE 2

Composition of Bulk and fractions.

| Size Category | NDF % | TDF % | Crude Protein % | Crude Fat % | TDN % |
|---|---|---|---|---|---|
| Original DDGS | 26.90 | 28.30 | 30.15 | 10.30 | 81.00 |
| B20 | 29.90 | 32.10 | 26.50 | 10.15 | 79.85 |
| B30 | 37.05 | 35.90 | 24.35 | 9.47 | 79.70 |
| B40 | 29.10 | 32.50 | 28.10 | 9.85 | 80.80 |
| B60 | 26.20 | 25.20 | 33.55 | 10.15 | 80.30 |
| Bpan | 17.20 | 19.40 | 38.20 | 11.70 | 82.15 |

NDF: Neutral Detergent Fiber;
TDF: Total Dietary Fiber;
TDN: Total Digestible Nutrients Significantly, sieving alone produced two size categories (B60 and BPan) that contained low fiber content while being enriched in protein and fat. These two fractions comprised about 40% of the mass of the original DDGS. The protein enhancement for BPan and B60 in comparison to the original DDGS are 26.7% and 11.3%, respectively. The reduction in NDF values for BPan and B60 in comparison to the original DDGS are 36.1% and 13.7% respectively.

Material obtained by sieving from the other three size categories (B20, B30 and B40), were each subjected to air elutriation at different velocities to determine: a) the yields at each velocity; b) the composition of residual and fiber fractions, and c) the desirable or optimum velocities for each size fraction.

TABLE 3

Results for B20 Size Category

| Velocity (in m/sec.) | Lighter Fraction Yield % | NDF % (Lighter) | NDF % (Bulk) | NDF % (Heavier) | Protein % (Lighter) | Protein % (Bulk) | Protein % (Heavier) | Fat % (Lighter) | Fat % (Bulk) | Fat % (Heavier) |
|---|---|---|---|---|---|---|---|---|---|---|
| 2.23 | 19.97 | 52.95 | 29.90 | 25.95 | 14.10 | 26.50 | 29.40 | 5.24 | 10.15 | 11.80 |
| 2.60 | 27.80 | 47.20 | 29.90 | 25.55 | 17.00 | 26.50 | 30.40 | 6.67 | 10.15 | 12.30 |
| 3.04 | 35.29 | 42.10 | 29.90 | 25.45 | 18.90 | 26.50 | 30.50 | 6.89 | 10.15 | 12.90 |
| 3.47 | 43.27 | 42.30 | 29.90 | 22.50 | 20.00 | 26.50 | 31.10 | 7.45 | 10.15 | 12.90 |
| 4.08 | 54.82 | 36.95 | 29.90 | 21.45 | 22.10 | 26.50 | 32.00 | 8.36 | 10.15 | 13.30 |

NDF: Neutral Detergent Fiber
Bulk: Bulk fraction retained on this screen size.
Lighter: Elutriated fraction
Heavier: Residual fraction.

Observations: For all velocities NDF % (Lighter)>NDF % (Bulk)>NDF % (Heavier), Protein % (Heavier)>Protein % (Bulk)>Protein % (Lighter) and Fat % (Heavier)>Fat % (Bulk)>Fat % (Lighter). This indicates the removal of fiber from the bulk and the enhancement of protein and fat in the heavier fraction.

Fiber vs. velocity: As velocity is increased, the mass of fiber (i.e. yield) removed from the bulk is higher, but the mass of non-fiber accompanying it is also higher (NDF % is lower). Thus, the amount of fiber produced is higher when the velocity is increased, but the purity of the fiber is lower.

Residual fraction vs. velocity: As velocity is increased, the fiber content in the residual fraction is lower (i.e. NDF % is lower) and the enhancement of protein and fat is higher (i.e. protein % and fat % are higher).

Optimum velocity. For high fiber removal, operating at 4.08 m/sec. or higher yields the highest amount of fiber and the highest enhancement of protein in the residual fraction. The yield of residual fraction, however, is reduced in that a lesser mass is realized. This velocity will be more desirable when the price of fiber is not a strong function of the purity of fiber, the price of residual fraction is a strong function of the protein/fat levels and fiber is much more valuable than the residual fraction.

For fiber purity and high mass of residual fraction, operating at 2.23 m/sec. or lower results in high purity fiber and a higher yield of residual fraction with low enhancement in protein. This velocity will be more desirable when the price of fiber is a strong function of the purity of fiber, the price of residual fraction is not a strong function of the protein/fat levels and fiber is much less valuable than the residual fraction.

Thus, a desirable or optimum velocity can be selected according to the relative prices of fiber and residual fraction, the dependence of the value of fiber on its purity and the dependence of the value of residual fraction on the protein/fat levels.

TABLE 4

Results for B30 Size Category

| Velocity (in m/sec.) | Lighter Fraction Yield % | NDF % (Lighter) | NDF % (Bulk) | NDF % (Heavier) | Protein % (Lighter) | Protein % (Bulk) | Protein % (Heavier) | Fat % (Lighter) | Fat % (Bulk) | Fat % (Heavier) |
|---|---|---|---|---|---|---|---|---|---|---|
| 1.84 | 18.83 | 58.70 | 37.05 | 28.70 | 9.88 | 24.35 | 27.80 | 5.10 | 9.47 | 11.60 |
| 2.06 | 33.78 | 52.00 | 37.05 | 28.50 | 14.40 | 24.35 | 29.40 | 5.96 | 9.47 | 12.40 |
| 2.23 | 40.41 | 48.15 | 37.05 | 26.10 | 16.60 | 24.35 | 29.90 | 6.30 | 9.47 | 13.10 |
| 2.41 | 50.02 | 46.10 | 37.05 | 25.35 | 18.60 | 24.35 | 30.60 | 6.93 | 9.47 | 13.60 |
| 2.83 | 72.92 | 37.30 | 37.05 | 23.70 | 22.40 | 24.35 | 31.20 | 8.11 | 9.47 | 15.70 |

Observations: Similar observations are applicable as indicated for the B20 size category, but the velocity range of experimentation was lower. The velocity range was between 1.84 m/sec. and 2.83 m/sec. A desirable or optimum velocity is selected according to the relative prices of fiber and residual fraction, the dependence of the value of fiber on its purity and the dependence of the value of residual fraction on the protein/fat levels.

TABLE 5

Results for B40 Size Category

| Velocity (in m/sec.) | Lighter Fraction Yield % | NDF % (Lighter) | NDF % (Bulk) | NDF % (Heavier) | Protein % (Lighter) | Protein % (Bulk) | Protein % (Heavier) | Fat % (Lighter) | Fat % (Bulk) | Fat % (Heavier) |
|---|---|---|---|---|---|---|---|---|---|---|
| 1.80 | 18.43 | 48.20 | 29.10 | 25.35 | 15.10 | 28.10 | 31.00 | 6.88 | 9.85 | 11.30 |
| 1.96 | 34.98 | 43.25 | 29.10 | 22.90 | 19.60 | 28.10 | 32.70 | 7.83 | 9.85 | 12.30 |
| 2.14 | 41.61 | 40.45 | 29.10 | 22.10 | 21.20 | 28.10 | 32.60 | 8.26 | 9.85 | 12.00 |
| 2.32 | 60.27 | 34.10 | 29.10 | 22.30 | 24.80 | 28.10 | 33.00 | 8.90 | 9.85 | 12.60 |

Observations from Table 5 results. Similar observations are indicated as those for the B20 and B30 size categories, but the velocity range of experimentation is lower, between 1.80 m/sec. and 2.32 m/sec. A desirable or optimum velocity is selected according to the relative prices of fiber and residual fraction, the dependence of the value of fiber on its purity and the dependence of the value of residual fraction on the protein/fat levels.

Products from the process. There are a total of eight fractions from this process: B20L, B20H, B30L, B30H, B40L, B40H, B60 and BPan. The L and H designate a lighter elutriated fraction and heavy elutriated fraction, respectively. A fiber-enriched combination is prepared comprising B20L, B30L and B40L. The remaining fractions (B20H, B30H, B40H, B60 and BPan) are optionally pooled or each can be an individual product.

The combinations for the residual products can be selected according to the dependence of the price of the residual fractions on the protein, fat, or protein and fat content. For example, if the price of the residuals were a strong function of the protein/fat level, then it is preferred to treat the residuals as individual products. Non-mixing can allow the extraction of maximum revenues from the high-protein/fat fractions. If the price of the residuals were not a strong function of the protein/fat level, then it can be preferred to mix the residuals in appropriate combinations in order to obtain maximum economic revenue.

For this commercial DDGS, the results of fiber removal and enhancement of protein/fat in residuals are shown in Table 6 and Table 7 for two possible scenarios: a) high fiber removal; and b) increased fiber purity and greater mass of residual fraction.

TABLE 6

Results at highest operated air velocity - high fiber removal and low mass of residuals.

| Size Category | Operating Velocity (m/sec.) | Yield % of Lighter | Protein % in bulk | Protein % in Heavier | Enhancement % in Protein (Bulk to Heavier) | Fat % in bulk | Fat % in heavier | Enhancement % in Fat (Bulk to Heavier) | NDF % of bulk | NDF % of Heavier | Reduction % in NDF (bulk to heavier) |
|---|---|---|---|---|---|---|---|---|---|---|---|
| B20 | 4.08 | 54.82 | 26.50 | 32.00 | 20.75 | 10.15 | 13.30 | 31.03 | 29.90 | 21.45 | 28.26 |
| B30 | 2.83 | 72.92 | 24.35 | 31.20 | 28.13 | 9.47 | 15.70 | 65.79 | 37.05 | 23.70 | 36.03 |
| B40 | 2.32 | 60.27 | 28.10 | 33.00 | 17.44 | 9.85 | 12.60 | 27.92 | 29.10 | 22.30 | 23.37 |
| B60 | — | — | 33.55 | — | — | 10.15 | — | — | 26.20 | — | — |
| Bpan | — | — | 38.20 | — | — | 11.70 | — | — | 17.20 | — | — |

TABLE 7

Results at lowest operated air velocity - high fiber purity and high mass of residuals.

| Size Category | Operating Velocity (m/sec.) | Yield % of Lighter | Protein % in bulk | Protein % in Heavier | Enhancement % in Protein (Bulk to Heavier) | Fat % in bulk | Fat % in heavier | Enhancement % in Fat (Bulk to Heavier) | NDF % of bulk | NDF % of Lighter | Enhancement % in NDF (bulk to lighter) |
|---|---|---|---|---|---|---|---|---|---|---|---|
| B20 | 2.23 | 19.97 | 26.50 | 29.40 | 10.94 | 10.15 | 11.80 | 16.26 | 29.90 | 52.95 | 77.09 |
| B30 | 1.84 | 18.83 | 24.35 | 27.80 | 14.17 | 9.47 | 11.60 | 22.49 | 37.05 | 58.70 | 58.43 |
| B40 | 1.80 | 18.43 | 28.10 | 31.00 | 10.32 | 9.85 | 11.30 | 14.72 | 29.10 | 48.20 | 65.64 |
| B60 | — | — | 33.55 | — | — | 10.15 | — | — | 26.20 | — | — |
| Bpan | — | — | 38.20 | — | — | 11.70 | — | — | 17.20 | — | — |

For this set of experiments, the values for velocities were dependent on the type of equipment used for elutriation. The velocity range was chosen such that the yield of lighter fraction was a minimum of about 15% (visually pure fraction) and a maximum of about 75%. These velocities are for an elutriation column with a diameter of 2.5 inches. The corresponding velocities for cyclones are expected to be higher.

Feed analysis results for NDF and protein content are generally considered to be reliable. Certain results for fat determinations had an error of up to about 5%.

Figure 5:
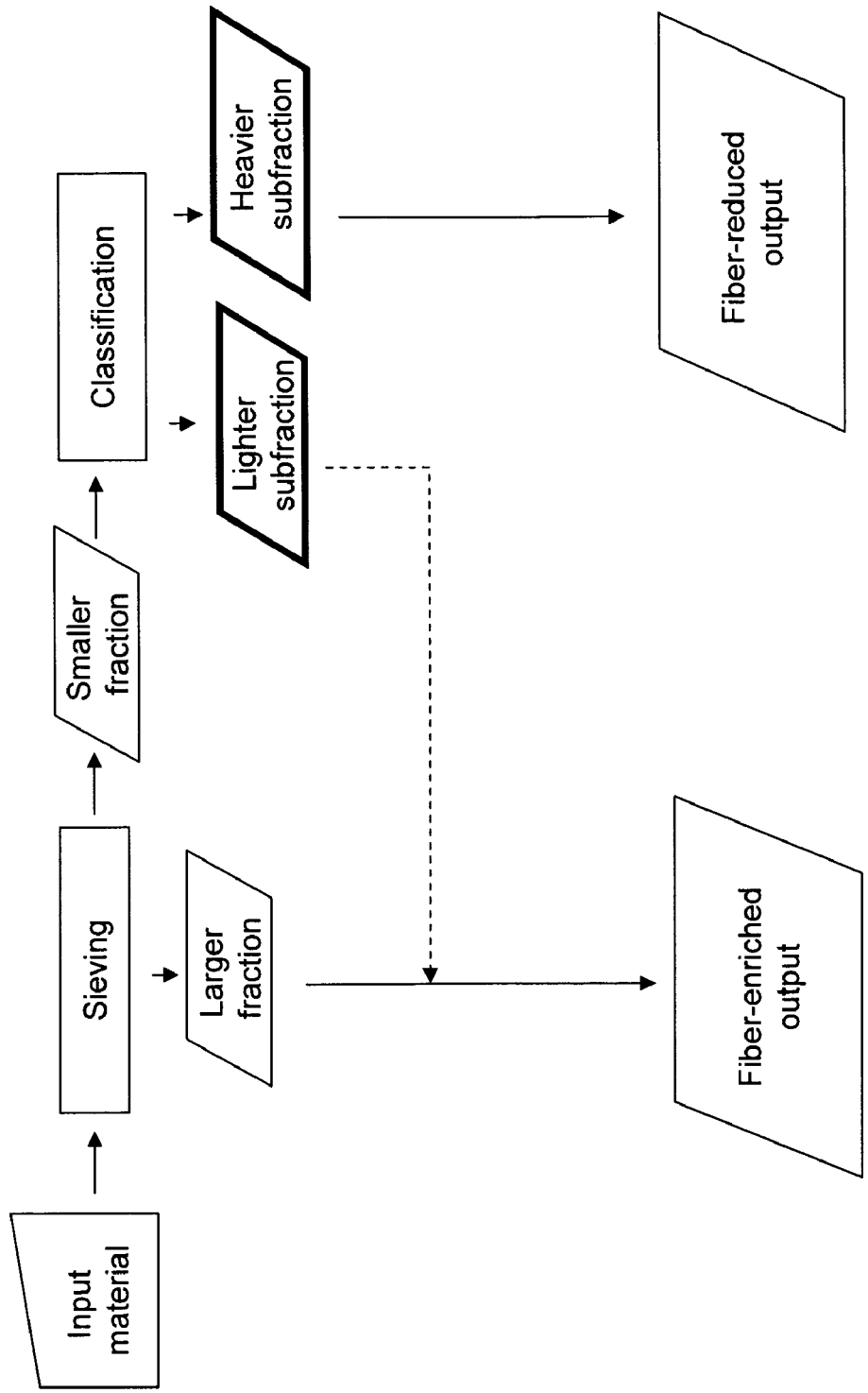
FIG. 5. Flowchart of fiber removal process with sieving then elutriation.

FIG. 5 further illustrates a flow chart of a fiber removal process. Input material is first subjected to sieving. This separates the input material into larger and smaller sized fractions. The smaller fraction is then treated by classification, such as by gravity air elutriation. Classification differentiates the smaller fraction into a lighter subfraction and a heavier subfraction. The initially sieved larger fraction and the classified lighter subfraction of the smaller fraction can be combined to yield a fiber-enriched output. The classified heavier fraction yields a non-fiber output. The initial smaller fraction itself can yield a non-fiber output. Optionally, classification can be performed on the larger fraction output of sieving or classification can be performed on both larger and smaller fractions.

In an embodiment where sieving precedes elutriation, it is not always necessarily true for every sieving technique or screen size that a sieved fraction of smaller particles will be reduced in fiber content relative to a reference starting material or bulk material. In some instances, it can be true that a given sieved fraction will be so reduced in fiber content. When original DDGS is first elutriated, though, an elutriated lighter fraction subjected to sieving will generally yield a sieved small particle size fraction having a lesser fiber content in comparison to the original DDGS starting material.

Certain material from industrial sources is often variable with respect to content. For instance, DDGS output from one ethanol plant to another or batches within an individual plant may vary considerably with respect to component proportion (protein, fat, or fiber content) and physical properties such as particle size. In a preferred embodiment, processing DDGS by first sieving followed by elutriation can effect an increased standardization of a fiber-reduced DDGS output and yield a more generally applicable method. In a highly preferred embodiment, when screening precedes elutriation there is a more robust process in that the fiber removal processing parameters are less dependent on variation in initial DDGS quality or composition.

In another embodiment, an initial sieving is performed on an input material such as DDGS to make the material more standardized or uniform by size for manipulation by further fiber removal process of elutriation and sieving. In this embodiment, the process can be summarized as sieving, elutriation, then sieving.

Example 8

Classifiers

Embodiments of the present invention can use a variety of classifying systems and apparatus capable of performing separation of a material based on particle size, density, shape, and/or weight. In particular, a gravity air elutriation system or apparatus is used. In embodiments, an air classification system can be selected from the following types: static cyclone, cyclone classifiers, single or multi-stage dynamic classifiers, cross-flow classifiers, spiral separators, high energy dispersion classifiers, and turbine classifiers (single and multiple wheel). In an embodiment, the system is an aspirator. An air classification system can be selected and adapted based on one or more properties of the input material. In an embodiment, a unit can depend on elutriation or centrifugal force or both. See C. C. Huang, 1996. In an embodiment, a unit can use a fluid other than air. In an embodiment, a fluid is nitrogen, steam, or water.

Example 9

Fiber from Processed Corn Products

Fiber removed or harvested from processes and devices of the invention is used or further characterized. Upon processing DDGS by the combination of classifying and sieving, a relatively pure fiber fraction is obtained. This corn fiber can be used to produce corn fiber gum and corn fiber oil. The corn fiber contains phytosterols which are known to have cholesterol-reducing properties. The fiber generated from the present invention can be used as a nutraceutical. Fiber generated from the present invention can be used as a laxative. Fiber made from the present invention can optionally be further processed such as by size fractionation or fractionation based on other properties.

Fiber generated from the invention can be used for power generation by combustion. Combustion, whether or not used in power generation, can produce fiber ash which can be used in the making of cement and other composites. Fiber ash can be used in producing soaps. Fiber from the invention can be used in producing textiles and paper products.

Example 10

Other Agricultural Products as Input Material

Embodiments of the invention are also applicable when other input materials are used. For example, another input material can be legumes (e.g. soybeans), barely, sorghum, wheat, or a product of each derived therefrom, respectively. In each case, process and device parameters are optimized regarding the physical properties of the input material. For example, an air velocity rate is optimized for elutriation of a sorghum product. Similarly, sieving parameters are optimized for sieving a sorghum product. Analogous customizations are made for a wheat product. For example, a sorghum or wheat product can be a processed product similar to DDGS produced from corn as the grain starting material.

A processed sorghum product is used as an input material. The input material is separated by particle size using a sieve parameter so as to effect separation of a larger particle size fraction and a smaller particle size fraction. The larger fraction, smaller fraction, or both larger and smaller fractions are then subjected to classification so as to effect separation of one or more fiber-enriched lighter fractions and one or more fiber-reduced heavier fractions.

A processed wheat product is used as an input material. The input material is separated by particle size using a sieve parameter so as to effect separation of a larger particle size fraction and a smaller particle size fraction. The larger fraction, smaller fraction, or both larger and smaller fractions are then subjected to classification so as to effect separation of one or more fiber-enriched lighter fractions and one or more fiber-reduced heavier fractions.

Example 11

Processing of DDGS

Abstract

A process was developed to separate fiber from distillers dried grains with solubles (DDGS) in a dry grind corn process. Separation of fiber from DDGS can provide two valuable coproducts: 1) DDGS with reduced fiber, increased fat and increased protein contents and 2) fiber. This process used two separation methods, sieving and elutriation, to separate the fiber. Material carried by air to the top of the elutriation column was called the "lighter fraction" and material that settled to the bottom of the column was called the "heavier fraction." We evaluated the compositions of fractions produced from sieving and elutriation. Two commercial samples of DDGS were obtained from two dry grind corn plants. Sieving over four screens (869, 582, 447 and 234 μm openings) created five size categories. The two smallest size categories contained >40% (w/w) of the original DDGS and had reduced fiber and increased protein and fat contents relative to the original DDGS. Elutriation of the remaining three size categories increased protein and fat contents and reduced fiber contents in the heavier fractions. Elutriation at air velocities between 1.59 and 5.24 m/s increased the protein content of the heavier fraction by 13 to 41% and increased the fat content of the heavier fraction by 4 to 127% compared to the bulk fractions of each size category. This process was effective in separating fiber from both DDGS samples evaluated. The process does not require changes in the existing dry grind process and can be implemented at the end of the dry grind process.

Introduction

In a dry grind corn plant, starch is fermented to ethanol. Remaining components in the corn, namely, protein, fiber, fat, unconverted starch and ash, form a coproduct known as distillers dried grains with solubles (DDGS). DDGS is defined as the product obtained after removal of ethyl alcohol by distillation from the yeast fermentation of a grain or a grain mixture by condensing and drying at least 75% of the resultant whole stillage (AAFCO 2002). Currently, dry grind corn plants produce about 70% of fuel ethanol in the US. Ethanol production in the US is expected to increase in the future (RFA 2004); DDGS supply will increase proportionally. Supply and demand of DDGS will play an important role in the economics of ethanol production. In the current scenario of rapidly increasing DDGS supply, there is a need for enhancing the value of DDGS. Separation of fiber from DDGS could result in two products: 1) DDGS with reduced fiber, increased fat and increased protein contents and 2) fiber.

DDGS with reduced fiber content could be used in nonruminant animal diets. DDGS with increased protein and fat content will enhance nutritional value and could increase market value. DDGS with high fat (13%) and high protein (33%) has a projected worth of about 5 to 20 dollars per ton more from a nutrient content basis than DDGS with lower fat (11%) and lower protein (28%) (Belyea et al 2004). Fiber produced from the process herein would be an additional coproduct of the dry grind plants. Corn fiber could be used to make valuable products such as corn fiber oil, corn fiber gum, bioethanol and xylitol (Anon 2002, Buchanan 2002, Grohmann et al 1997, Moreau et al 1999).

Singh et al (2002) investigated air aspiration as a method to separate fiber from DDGS. They showed limited success for aspiration in recovering fiber from DDGS and in recovering phytosterol compounds. In the present study, we used a combination of two separation methods, sieving and elutriation, to separate fiber from DDGS. This process can be referred to as the Elusieve™ process. Elutriation is defined as the separation of particles by means of an upward flowing stream of fluid. Aspiration is defined as "the act or the result of removing, carrying along, or drawing by suction" (McGraw-Hill 1978). The term "aspiration" is commonly used in the cereal processing industry to refer to the separation of particles by means of a stream of air, regardless of the method used to generate the flow of fluid. In this study, a blower was used to produce an upward stream of air and hence "elutriation" is used in this example instead of "aspiration". For industrial applications of this process, equipments such as aspirators and cyclones may be used. The term "classification" as understood in the industrial art is also relevant for elutriation techniques.

Sieving is used to separate particles based on the difference in size. Elutriation by air is used to separate the particles in DDGS based on combined effects of density, shape and size characteristics. In dry milling process, fiber is separated from other components of corn based on its lower density. Fiber would be less dense than nonfiber components in DDGS. When air is passed through DDGS, fiber would be carried away. Some nonfiber also would get carried with the air because nonfiber particles that are more dense and have smaller size would experience the same forces as fiber particles that are less dense and have larger size.

Fiber in the original DDGS spans a wide range of sizes, and hence elutriation of DDGS would selectively remove fiber having a size that can be carried by the air at the operating velocity. At high air velocities, air would carry fiber of all sizes, but the carry over of nonfiber material would be high. Hence, it could be effective to first sieve the DDGS into various size categories and then elutriate the material in each size category at appropriate velocities to separate fiber from each size category. Objectives of this study were to: 1) determine the composition and other nutritional characteristics of fractions produced after sieving and elutriation steps and 2) assess the effect of velocity of air on composition and yield of lighter fractions.

Materials and Methods

DDGS samples (20 kg) were obtained from two dry grind corn plants in the United States. The dry grind corn plants used only corn as their feedstock. DDGS 1 was produced from a flash drying process. DDGS 2 was produced from a ring drying process. In a flash dryer the wet feed is dried by transporting it for a few seconds in a hot gas stream. A Ring dryer contains a centrifugal classifier in the flash drying loop that recirculates larger, wetter particles back for further drying.

Sieving. A vibratory screen (Model LS188333, SWECO Vibro-Energy Separator, Los Angeles, Calif.) was used to sieve DDGS samples into size categories. The screens were: 24T (869 μm), 34T (582 μm), 35M (447 μm), 60M (234 μm) and pan. The letters "M" and "T" refer to market grade cloth and tensil bolt cloth. The size categories of material retained on these screens are referred to as 24T, 34T, 35M, 60M and Pan, based on their respective screen labels. One kilogram of material was sieved on each screen for 2 hr. The completion of sieving was ensured by measuring the weight change in the receiving container. The material passing through the sieve with a larger opening was collected and then fed to the next smaller sieve size. Only one sieve was used at a time.

Elutriation. An elutriation apparatus (FIG. 7) was developed for separating fiber from DDGS. The apparatus had an elutriation column, an air blower for supplying air to the elutriation column, a surge box mechanism for controlling airflow, a vibratory feeder for feeding material into the column and collection vessels for receiving the lighter and heavier fractions. Material elutriated by the air was called "lighter fraction." Material that settled to the bottom of the elutriation column was called "heavier fraction." The elutriation column was constructed using transparent perspex material to be able to visualize the separation process. The internal diameter of the column was 63 mm and the distance from the powder inlet to the air inlet nozzle was 360 mm. The distance of lighter fraction collection vessel from the powder inlet was 1100 mm. The lighter fraction collection vessel (300×300× 300 mm) was constructed of transparent perspex material and had a hole (66 mm diameter) in the center of the bottom plate to insert the vessel onto the elutriation column. During operation, the open top was covered to 95% of its area using a wooden sheet. The velocity of airflow was measured by inserting a hotwire anemometer (Model 8355, TSI Velocicalc, St. Paul, Minn.) into the powder inlet nozzle, with a set time constant of 10 sec. The anemometer was calibrated using a wind tunnel (Model 8390, TSI, St. Paul, Minn.). Diameter of the air inlet was 63 mm and the diameter of the powder inlet was 19 mm. The air was supplied using a blower (Model 2C701, 61W Dayton, Chicago, Ill.). Airflow was controlled by a sliding plate arrangement on top of a cubical wooden box that was used as a surge vessel for the air supply. The air flow through the elutriation column is in the turbulent regime for the range of flowrate used in this study. DDGS material was fed into the elutriation column by a vibratory feeder (Model 3090, POWDERTEC sample mill, Germany) at a rate of 1.0 g/min.

Experimental procedure. Elutriation of each size category was carried out at four different velocities. The velocity range was selected such that the yield of lighter fraction was a minimum of 15% and a maximum of 90%. Air velocities varied between 1.59 and 5.24 m/s, depending on DDGS material characteristics and size category.

Analytical Tests. Chemical analyses were carried out at a commercial analytical laboratory. Protein was reported as 6.25 times total nitrogen. Samples were analyzed for crude protein (AOAC 2003, Method: 990.03), crude fat (AOAC 2003, Method: 920.39), ash (AOAC 2003, Method: 942.05), crude fiber (AOAC 2003, Method: 962.09) and acid detergent fiber (AOAC 2003, Method: 973.18). Neutral detergent fiber (NDF) content was determined by the procedure outlined by Van Soest et al (1991). Crude fiber is the residue remaining after extraction by acid and alkaline hydrolysis, NDF is a measure of the cellulose, hemicellulose and lignin contents, while acid detergent fiber (ADF) is a measure of cellulose, acid detergent insoluble nitrogen, acid insoluble ash and lignin contents (Van Soest et al 1991). Sample moisture contents were determined using the two stage convection oven method (AACC 2000, Method: 44-18).

Total digestible nutrients (TDN %) was calculated using digestive factors of 0.78, 1.90, 0.57 and 0.85 for protein, fat, fiber and nitrogen free extract, respectively and was calculated as (NRC 1982): TDN %={(% crude protein*0.78)+(% crude fat*1.90)+(% crude fiber*0.57)+(% nitrogen free extract*0.85)}

Metabolizable energy (ME, in Mcal/kg) was calculated as: ME={0.96−(0.00202*% crude protein)}*TDN*0.02/0.4536

Net energy gain (NEg, Mcal/kg) was calculated as: NEg={(0.00786*% TDN)−0.051}/0.4536

NDF separation factor. A Neutral Detergent Fiber Separation Factor for elutriation is defined as the ratio of the NDF %/Non-NDF % of the lighter fraction to the NDF %/Non-NDF % of the heavier fraction. The NDF separation factor is denoted with the letter Q and calculated as:

$$Q = [\text{NDF \%}/(100-\text{NDF \%})]_{Lighter\ fraction} / [\text{NDF \%}/(100-\text{NDF \%})]_{Heavier\ fraction}$$

NDF separation factor (Q) indicates the selectivity of air in carrying fiber rather than nonfiber at the operating air velocity. A high NDF separation factor, Q, indicates that the selectivity of air in carrying fiber is high. NDF separation factor is analogous to solvent selectivity in liquid extraction and relative volatility in distillation (Treybal 1980).

Statistical Analyses. The repeatability of the elutriation experiments was verified. Elutriation of DDGS 1 24T size category was carried out five times at an air velocity of 2.47 m/s and powder feeding rate of 1 g/min. Mean yield of lighter fraction obtained was 16.7% with a coefficient of variation of □2.5%. Elutriation of DDGS 2 35M size category was carried out five times at an air velocity of 1.59 m/s and powder feeding rate of 1 g/min. Mean yield of lighter fraction obtained was 16.8% with a coefficient of variation of +/−9.9%. All composition values are reported as the mean of two determinations taken from the same lot of material.

Results and Discussion

Sieving. The two smallest size categories, 60M (234 447 μm) and Pan (<234 μm), which were produced by sieving of the original DDGS samples, comprised 40% of the mass of the original DDGS for DDGS 1 and 57% of the mass of the original DDGS for DDGS 2 (Table 9). 60M and Pan size categories contained lower fiber and higher protein contents with respect to the original DDGS samples (Tables 10 and 11).

TABLE 9

Weight percent of material retained on each screen.

| Mesh Category | Opening in μm | Referred to as | DDGS-1: % (w/w) retained on screen | DDGS-2: % (w/w) retained on screen |
|---|---|---|---|---|
| 24T | 869 | 24T | 27.0 | 12.7 |
| 34T | 582 | 34T | 19.4 | 16.9 |
| 35M | 447 | 35M | 13.3 | 13.3 |
| 60M | 234 | 60M | 20.1 | 30.1 |
| Pan | 0 | Pan | 20.2 | 27.0 |

TABLE 10

Composition (dry basis) of original material and size categories of DDGS 1 after sieving.

| Size Category | Nominal particle size (μm) | Crude Protein % | Crude Fat % | TDN % | Ash % | NDF % | Crude Fiber % | ADF % | NEg (Mcal/kg) | ME (Mcal/kg) |
|---|---|---|---|---|---|---|---|---|---|---|
| Original Material | All | 33.6 | 12.5 | 90.7 | 3.95 | 32.5 | 11.5 | 18.7 | 1.46 | 3.57 |

TABLE 10-continued

Composition (dry basis) of original material and size categories of DDGS 1 after sieving.

| Size Category | Nominal particle size (μm) | Crude Protein % | Crude Fat % | TDN % | Ash % | NDF % | Crude Fiber % | ADF % | NEg (Mcal/kg) | ME (Mcal/kg) |
|---|---|---|---|---|---|---|---|---|---|---|
| 24T | >869 | 29.3 | 12.5 | 89.5 | 3.95 | 33.4 | 11.5 | 15.2 | 1.46 | 3.57 |
| 34T | 582 to 869 | 26.9 | 11.3 | 88.8 | 4.15 | 37.8 | 9.25 | 15.3 | 1.43 | 3.55 |
| 35M | 447 to 582 | 31.2 | 10.9 | 89.8 | 4.14 | 33.6 | 10.1 | 17.1 | 1.46 | 3.55 |
| 60M | 234 to 447 | 37.5 | 11.3 | 89.7 | 4.33 | 29.3 | 7.75 | 19.6 | 1.46 | 3.51 |
| Pan | <234 | 42.2 | 12.9 | 90.9 | 4.57 | 19.0 | 6.12 | 14.3 | 1.48 | 3.51 |

TDN—Total digestible nutrients,
NDF—Neutral detergent fiber,
ADF—Acid detergent fiber,
NEg—Net energy gain,
ME—Metabolizable energy

TABLE 11

Composition (dry basis) of original material and size categories for DDGS 2 after sieving.

| Size Category | Nominal particle size (μm) | Crude Protein % | Crude Fat % | TDN % | Ash % | NDF % | Crude Fiber % | ADF % | NEg (Mcal/kg) | ME (Mcal/kg) |
|---|---|---|---|---|---|---|---|---|---|---|
| Original Material | All | 32.9 | 13.2 | 91.0 | 4.53 | 33.6 | 8.90 | 13.9 | 1.48 | 3.59 |
| 24T | >869 | 21.2 | 13.1 | 90.3 | 4.09 | 39.0 | 12.6 | 15.5 | 1.46 | 3.66 |
| 34T | 582 to 869 | 24.1 | 11.9 | 90.0 | 3.30 | 40.1 | 10.7 | 15.9 | 1.46 | 3.64 |
| 35M | 447 to 582 | 27.5 | 12.7 | 90.3 | 4.32 | 34.5 | 8.60 | 13.4 | 1.46 | 3.62 |
| 60M | 234 to 447 | 33.6 | 12.5 | 89.3 | 4.80 | 29.7 | 8.55 | 11.5 | 1.46 | 3.51 |
| Pan | <234 | 40.1 | 13.3 | 90.9 | 4.70 | 27.9 | 4.35 | 10.8 | 1.48 | 3.53 |

TDN—Total digestible nutrients,
NDF—Neutral detergent fiber,
ADF—Acid detergent fiber,
NEg—Net energy gain,
ME—Metabolizable energy For DDGS 1, the original material contained 33.6% protein and 32.5% NDF; the 60M size category contained 37.5% protein and 29.3% NDF. The Pan size category contained 42.2% protein and 19.0% NDF (Table 10). For DDGS 2, the original material contained 32.9% protein and 33.6% NDF; the 60M size category contained 33.6% protein and 29.7% NDF. The Pan size category contained 40.1% protein and 27.9% NDF (Table 11). These two size categories (60M and Pan) of DDGS 1 and DDGS 2 were not subjected to elutriation due to low fiber and high protein contents.

Elutriation—fiber separation. To determine yields of lighter fraction at each velocity and compositions of lighter and heavier fractions, the three largest size categories, 24T (>869 μm), 34T (583-869 μm) and 35M (447-583 μm), were each subjected to air elutriation at different velocities. High NDF in the lighter fractions in conjunction with high protein and fat content in the heavier fractions signify effective separation of fiber from the bulk of each size category subjected to elutriation. For both DDGS samples, elutriation using air was effective in separating fiber from the bulk material of each size category (Table 12 for DDGS 1 and Table 13 for DDGS 2). For example, for the bulk material in the 35M size category of DDGS 1 and air velocity of 2.03 m/s, NDF increased from 33.6 to 51.4% in the lighter fraction, protein increased from 31.2 to 36.2% in the heavier fraction, and fat increased from 10.9 to 13.3% in the heavier fraction (Table 12). For the bulk material in the 34T size category of DDGS 2 and air velocity of 2.55 m/s, NDF increased from 40.1 to 54.6% in the lighter fraction, protein increased from 24.1 to 32.7% in the heavier fraction and fat increased from 11.9 to 18.8% in the heavier fraction (Table 13).

TABLE 12

Compositions (dry basis) of fractions from elutriation of DDGS 1 that demonstrate separation of fiber.

| Size category | Air velocity (m/s) | Yield % (L) | Crude Protein % (H) | Crude Fat % (H) | NDF % (L) | NDF % (H) |
|---|---|---|---|---|---|---|
| 24T | 0* | — | 29.3* | 12.5* | — | 33.4* |
| (Size > 869 μm) | 2.47 | 17.20 | 33.0 | 13.0 | 62.8 | 31.4 |
| | 3.35 | 27.80 | 35.6 | 14.2 | 53.3 | 32.6 |
| | 4.45 | 43.30 | 41.2 | 15.5 | 46.8 | 24.2 |
| | 5.24 | 61.68 | 35.5 | 16.4 | 42.3 | 27.6 |
| 34T | 0* | — | 26.9* | 11.3* | — | 37.8* |

TABLE 12-continued

Compositions (dry basis) of fractions from elutriation of DDGS 1 that demonstrate separation of fiber.

| Size category | Air velocity (m/s) | Yield % (L) | Crude Protein % (H) | Crude Fat % (H) | NDF % (L) | NDF % (H) |
|---|---|---|---|---|---|---|
| (582 μm < Size < 869 μm) | 2.22 | 23.13 | 32.0 | 12.6 | 62.7 | 34.5 |
| | 2.55 | 33.40 | 33.1 | 13.8 | 58.7 | 32.4 |
| | 2.85 | 52.82 | 34.9 | 16.2 | 48.1 | 31.6 |
| | 3.86 | 82.30 | 35.5 | 16.3 | 41.3 | 26.2 |
| 35M | 0* | — | 31.2* | 10.9* | — | 33.6* |
| (447 μm < Size < 582 μm) | 1.84 | 19.30 | 35.4 | 13.1 | 56.0 | 27.6 |
| | 2.03 | 31.80 | 36.2 | 13.3 | 51.4 | 28.3 |
| | 2.22 | 47.10 | 36.5 | 14.1 | 44.3 | 26.9 |
| | 2.60 | 75.98 | 37.1 | 15.4 | 39.3 | 25.8 |

*Values at 0 m/s denote initial bulk material,
NDF—Neutral detergent fiber,
H—Heavier fraction,
L—Lighter fraction.

TABLE 13

Compositions (dry basis) of fractions from elutriation of DDGS 2 that demonstrate separation of fiber.

| Size category | Velocity (m/s) | Yield % (L) | Crude Protein % (H) | Crude Fat % (H) | NDF % (L) | NDF % (H) |
|---|---|---|---|---|---|---|
| 24T | 0* | — | 21.2* | 13.1* | — | 39.0* |
| (Size > 869 μm) | 2.55 | 21.20 | 25.6 | 17.1 | 66.2 | 32.2 |
| | 3.35 | 45.82 | 26.7 | 20.1 | 50.0 | 37.2 |
| | 4.45 | 68.52 | 25.5 | 24.7 | 45.2 | 37.7 |
| | 4.80 | 89.44 | 24.9 | 24.7 | 45.3 | 33.4 |
| 34T | 0* | — | 24.1* | 11.9* | — | 40.1* |
| (582 μm < Size < 869 μm) | 2.09 | 21.22 | 29.6 | 13.8 | 67.1 | 35.2 |
| | 2.55 | 41.93 | 32.7 | 18.8 | 54.6 | 32.7 |
| | 2.85 | 58.45 | 31.4 | 18.6 | 50.9 | 29.3 |
| | 3.60 | 88.21 | 29.9 | 27.0 | 43.8 | 25.7 |
| 35M | 0* | — | 27.5* | 12.7* | — | 34.5* |
| (447 μm < Size < 582 μm) | 1.59 | 18.22 | 32.1 | 13.4 | 61.2 | 28.5 |
| | 2.03 | 40.10 | 33.7 | 15.1 | 55.8 | 32.7 |
| | 2.22 | 46.30 | 33.6 | 15.3 | 52.4 | 29.7 |
| | 2.72 | 88.40 | 32.8 | 18.1 | 41.9 | 26.7 |

*Values at 0 m/s denote initial bulk material,
NDF—Neutral detergent fiber,
H—Heavier fraction,
L—Lighter fraction.

The relative values of NDF, protein, and fat contents in the fractions at each air velocity signify the separation of fiber, at all air velocities:

NDF % (lighter fraction)>NDF % (bulk)>NDF % (heavier fraction);

protein % (heavier fraction)>protein % (bulk)>protein % (lighter fraction); and fat % (heavier fraction)>fat % (bulk)>fat % (lighter fraction).

See Tables 12, 13, 14, and 15. Higher NDF content in the lighter fraction and higher protein and fat contents in the heavier fraction indicates that the combination of sieving and elutriation was effective in separating fiber from DDGS produced by two different drying methods (flash drying and ring drying). There were corresponding increases in protein and fat contents in the heavier fractions from DDGS 1 and DDGS 2.

Figure 19:
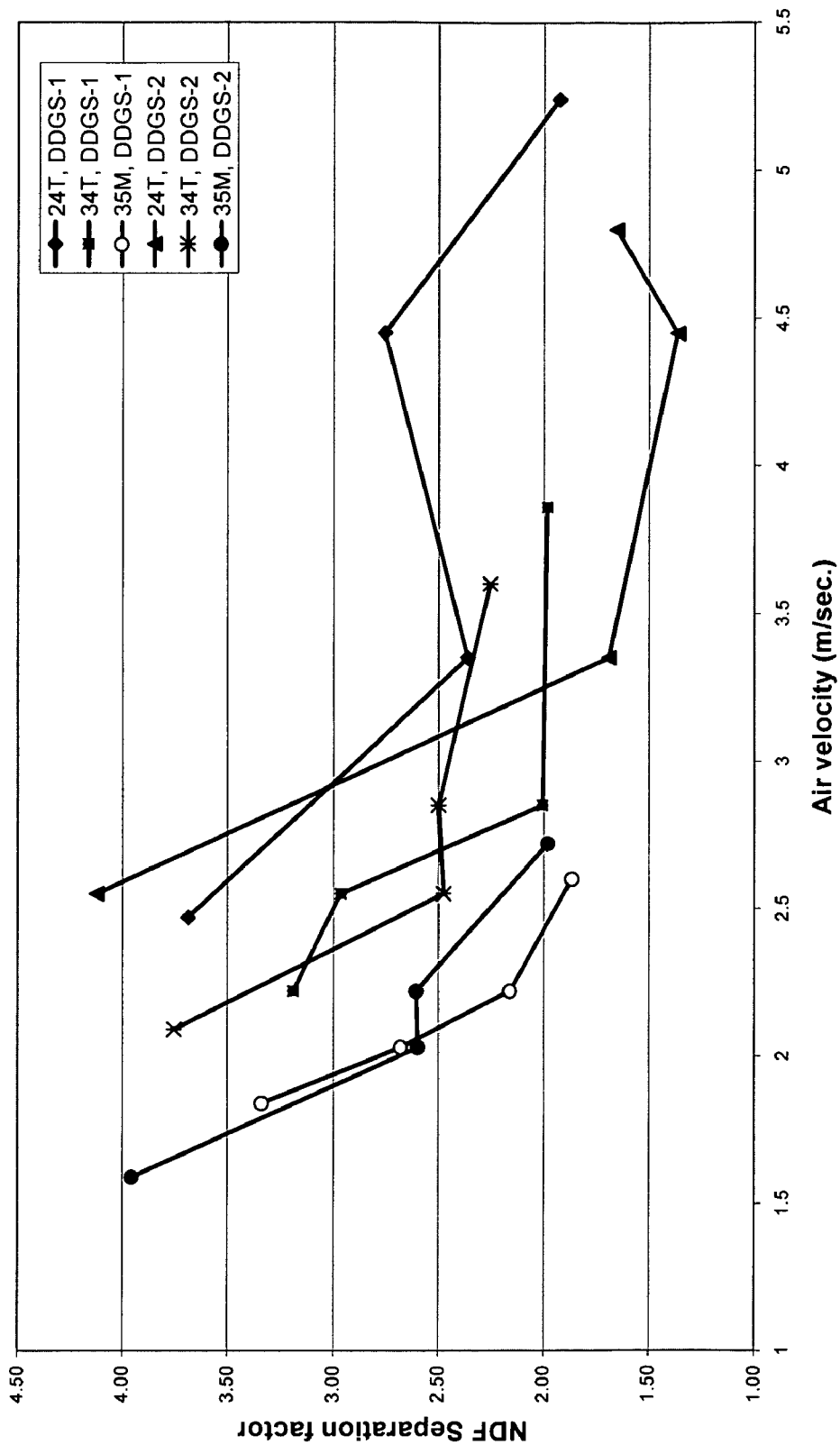
FIG. 19. Graph of NDF separation factors at different elutriation air velocities for elutriation of 24T, 34T and 35M size categories of samples DDGS-1 and DDGS-2.

Elutriation—effect of air velocity on fiber separation. An increase in air velocity increased the mass of lighter fraction and reduced the mass of heavier fraction. Correspondingly, protein and fat were higher in the heavier fraction and NDF was lower in the lighter fraction because higher air velocities carried the denser nonfiber components into the lighter fraction (Tables 12 and 13). In general, an increase in air velocity reduced the NDF separation factors obtained by elutriating the size categories which signifies reduced selectivity of the air in carrying fiber because of the ability of air to carry the denser nonfiber components at higher velocities (FIG. 19).

In general, protein contents of heavier fractions exhibited an increasing trend with increasing air velocity except for some size categories of both DDGS 1 and DDGS 2; protein contents of heavier fractions tended to become constant or reduce at high air velocities (Tables 12 and 13). The fat contents of heavier fractions for all size categories showed an increasing trend as air velocity was increased (Tables 12 and 13).

In a dry grind corn plant, the economically optimum air velocities for each size category may be governed by the dependence of fiber value on fiber purity and the dependence of the value of remaining DDGS on protein and fat contents. At low air velocities, fiber separated from the bulk material would have high NDF % (high purity of fiber), but the remaining DDGS would have lower protein and fat contents. At high air velocities, fiber separated from the bulk material would have low NDF % (low fiber purity), but the remaining DDGS would have higher protein and fat contents.

We explored whether a decrease in size of particles fed to the elutriation column could allow a decrease in the air velocity needed to produce a specific yield of lighter fraction as the force needed to carry smaller particles would be lower, density and shape remaining constant. Results from Tables 12 and 13 show that such a decrease in particle size does allow a decreased air velocity while obtaining a desired specific yield of lighter fraction. As the size of bulk material fed to the elutriation column decreased, operating air velocity needed to produce the same yield of lighter fraction decreased. For the size category with size greater than 869 μm of DDGS 1, the yield of lighter fraction at the air velocity of 2.47 m/s was 17.2% (Table 12). For the size category with size between 447 μm and 582 μm of DDGS 1, the air velocity needed to produce a similar yield (19.3%) was 1.84 m/s (Table 12), which was lower than the operating air velocity for 24T size category.

Elutriation—other characteristics of fractions. Crude fiber in the lighter fractions decreased as air velocity increased, exhibiting a similar trend as that of NDF, while ADF values did not follow any specific trend (Tables 14 and 15). TDN in the heavier fractions increased with increasing air velocity, exhibiting a trend similar to those of protein and fat contents in the heavier fractions, while there was no specific trend observed in the ash content, NEg (net energy gain) and ME (metabolizable energy) values for heavier as well lighter fractions (Tables 14 and 15).

TABLE 14

Other characteristics (dry basis) of fractions from elutriation of DDGS-1.

| Size category | Velocity (m/s) | Crude Protein % (L) | Crude Fat % (L) | Crude Fiber % H | Crude Fiber % L | ADF % H | ADF % L | TDN % H | TDN % L | Ash % H | Ash % L | NEg (Mcal/kg) H | NEg (Mcal/kg) L | ME (Mcal/kg) H | ME (Mcal/kg) L |
|---|---|---|---|---|---|---|---|---|---|---|---|---|---|---|---|
| 24T | 2.47 | 13.0 | 5.28 | 5.95 | 14.8 | 16.8 | 16.5 | 91.4 | 82.5 | 3.87 | 3.53 | 1.48 | 1.32 | 3.62 | 3.40 |
|  | 3.35 | 19.3 | 7.05 | 7.70 | 12.8 | 18.0 | 19.4 | 91.9 | 84.4 | 3.98 | 3.62 | 1.48 | 1.34 | 3.59 | 3.44 |
|  | 4.45 | 23.2 | 14.9 | 7.00 | 11.5 | 22.5 | 20.6 | 92.6 | 92.5 | 4.56 | 3.83 | 1.50 | 1.50 | 3.59 | 3.73 |
|  | 5.24 | 26.1 | 10.2 | 4.55 | 9.60 | 18.0 | 15.6 | 95.1 | 88.1 | 3.93 | 3.69 | 1.54 | 1.41 | 3.73 | 3.53 |
| 34T | 2.22 | 12.2 | 5.66 | 8.70 | 13.4 | 18.2 | 18.4 | 90.0 | 83.0 | 4.23 | 3.85 | 1.46 | 1.32 | 3.55 | 3.42 |
|  | 2.55 | 15.5 | 6.45 | 10.6 | 15.6 | 18.8 | 18.3 | 90.5 | 83.1 | 4.31 | 3.78 | 1.46 | 1.32 | 3.57 | 3.42 |
|  | 2.85 | 21.7 | 7.93 | 9.15 | 11.6 | 17.2 | 18.0 | 92.8 | 85.1 | 4.88 | 4.04 | 1.50 | 1.37 | 3.64 | 3.44 |
|  | 3.86 | 26.2 | 10.3 | 11.5 | 9.60 | 20.9 | 18.8 | 81.8 | 87.7 | 4.80 | 4.19 | 1.32 | 1.41 | 3.22 | 3.53 |
| 35M | 1.84 | 16.5 | 8.46 | 7.10 | 13.7 | 18.9 | 17.3 | 90.4 | 85.6 | 4.66 | 3.89 | 1.46 | 1.37 | 3.55 | 3.51 |
|  | 2.03 | 23.0 | 8.30 | 8.40 | 10.8 | 18.3 | 18.7 | 90.0 | 85.5 | 4.74 | 4.17 | 1.46 | 1.37 | 3.53 | 3.44 |
|  | 2.22 | 25.3 | 9.19 | 6.80 | 11.1 | 17.7 | 19.0 | 91.5 | 86.2 | 4.55 | 4.13 | 1.48 | 1.39 | 3.57 | 3.46 |
|  | 2.60 | 28.8 | 10.4 | 6.50 | 9.70 | 14.6 | 17.9 | 92.6 | 87.6 | 4.90 | 4.30 | 1.50 | 1.41 | 3.62 | 3.48 |

ADF—Acid detergent fiber,
TDN—Total digestible nutrients,
NEg—Net energy gain,
ME—Metabolizable energy,
H—Heavier fraction,
L—Lighter fraction.

TABLE 15

Other characteristics (dry basis) of fractions from elutriation of DDGS-2.

| Size category | Velocity (m/s) | Crude Protein % (L) | Crude Fat % (L) | Crude Fiber % H | Crude Fiber % L | ADF % H | ADF % L | TDN % H | TDN % L | Ash % H | Ash % L | NEg (Mcal/kg) H | NEg (Mcal/kg) L | ME (Mcal/kg) H | ME (Mcal/kg) L |
|---|---|---|---|---|---|---|---|---|---|---|---|---|---|---|---|
| 24T | 2.55 | 10.7 | 4.83 | 12.6 | 16.5 | 13.9 | 17.5 | 93.9 | 81.4 | 4.46 | 3.89 | 1.52 | 1.30 | 3.77 | 3.37 |
|  | 3.35 | 18.5 | 7.13 | 14.5 | 12.1 | 18.2 | 16.2 | 96.2 | 84.3 | 4.67 | 4.07 | 1.57 | 1.34 | 3.86 | 3.44 |
|  | 4.45 | 20.7 | 8.88 | 12.5 | 13.4 | 17.5 | 16.3 | 101 | 85.7 | 4.98 | 4.03 | 1.65 | 1.37 | 4.08 | 3.48 |
|  | 4.80 | 21.8 | 11.9 | 7.35 | 8.85 | 16.5 | 15.6 | 103 | 89.9 | 4.43 | 4.29 | 1.68 | 1.46 | 4.17 | 3.64 |
| 34T | 2.09 | 11.5 | 5.35 | 9.20 | 15.9 | 14.4 | 18.3 | 90.7 | 81.9 | 4.89 | 4.07 | 1.48 | 1.30 | 3.62 | 3.40 |
|  | 2.55 | 17.5 | 7.33 | 7.90 | 12.6 | 14.8 | 18.7 | 95.9 | 84.5 | 5.16 | 3.98 | 1.57 | 1.34 | 3.79 | 3.44 |
|  | 2.85 | 20.5 | 8.43 | 7.35 | 14.1 | 13.7 | 16.6 | 95.8 | 84.9 | 5.17 | 4.20 | 1.54 | 1.37 | 3.79 | 3.44 |
|  | 3.60 | 24.8 | 10.9 | 9.40 | 11.6 | 17.3 | 16.5 | 104 | 87.7 | 5.32 | 4.46 | 1.70 | 1.41 | 4.14 | 3.53 |
| 35M | 1.59 | 12.3 | 6.02 | 6.70 | 12.7 | 11.8 | 17.1 | 91.2 | 84.0 | 4.47 | 3.34 | 1.48 | 1.34 | 3.62 | 3.46 |
|  | 2.03 | 18.6 | 8.33 | 6.55 | 12.0 | 12.4 | 15.0 | 92.8 | 85.5 | 4.62 | 4.21 | 1.50 | 1.37 | 3.66 | 3.48 |
|  | 2.22 | 20.8 | 9.00 | 6.00 | 10.5 | 15.4 | 15.7 | 92.9 | 86.6 | 4.89 | 3.99 | 1.50 | 1.39 | 3.66 | 3.53 |
|  | 2.72 | 26.5 | 11.4 | 4.90 | 8.30 | 16.7 | 15.4 | 96.4 | 89.3 | 4.61 | 4.01 | 1.57 | 1.43 | 3.81 | 3.57 |

ADF—Acid detergent fiber,
TDN—Total digestible nutrients,
NEg—Net energy gain,
ME—Metabolizable energy,
H—Heavier fraction,
L—Lighter fraction.

CONCLUSIONS

Our process was effective in separating fiber from DDGS. Sieving alone produced two size categories that contained reduced fiber and increased contents of protein and fat. Elutriation of screened fractions resulted in increased contents of protein and fat and reduced fiber in the heavier fractions. Higher protein and fat content can increase the utility and market value of these DDGS fractions, and decreased fiber content can increase the inclusion levels and species compatibility for DDGS in nonruminant diets. Fiber produced from the process is an additional coproduct and can further increase applications (and projected revenues) because of its potential use in ruminant diets, production of corn fiber gum, corn fiber oil, phytosterols, xylitol and bioethanol.

The process and its products benefit dry grind corn processors, especially important in the current scenario of rapidly increasing ethanol production. This separation process does not require changes in the existing dry grind corn process and hence facilitates implementation in existing plants.

We briefly evaluated a speculative economic projection relating to fiber removal from distillers dried grains with solubles (DDGS) using sieving and elutriation. These projections are based in part on testing of two commercial samples of DDGS (DDGS 1 and DDGS 2). Sieving over four screens (869, 582, 447 and 234 micron openings) created five size categories. The two smallest size categories contained reduced fiber relative to the original DDGS. Elutriation of the remaining three size categories was effective in removing fiber and increased protein and fat contents in the residual DDGS. Economic analysis of the process was conducted based on removal of 20% of fiber fraction from the three largest size categories. Based on previous results, 20% removal of fiber from DDGS can increase the protein content of DDGS-1 and DDGS-2 samples by 8.5% and 7.0%, respectively. The dependence of price of feeds on their protein content was determined based on the 2003-2004 prices of feeds reported in Feed Outlook Report (2005), Economic Research Service, USDA. Based on assumptions of an 80,000 bushels/day dry grind corn plant and a price of 4.41 cents/kg (2 cents/lb) for fiber, the projected potential increase in revenue due to a process of the invention compared to the original unprocessed DDGS could provide a substantial economic benefit per operating day.

LITERATURE CITED

AACC. 2000. Approved Methods of the MCC, 10th ed. The American Association of Cereal Chemists: St Paul, Minn.

AAFCO. 2002. Official publication of AAFCO. The Association of American Feed Control Officials Incorporated: Oxford, Ind.

Anon. 2002. Microbial production of xylitol from corn fiber. Industrial Bioprocessing 24:5.

AOAC. 2003. Official methods of the AOAC, 17th ed. The Association of Official Analytical Chemists: Gaithersburg, Md.

Belyea, R. L., Rausch, K. D. and Tumbleson, M. E. 2004. Composition of corn and distillers dried grains with solubles from dry grind ethanol processing. Bioresource Technology 94:293-298.

Buchanan, C. M. 2002. High value products from corn fiber. Industrial Bioprocessing 24:3-4.

Grohmann, K. and Bothast, R. J. 1997. Saccharification of corn fiber by combined treatment with dilute sulphuric acid and enzymes. Process Biochem. 32:405-415.

McGraw-Hill. 1978. McGraw-Hill Dictionary of Scientific and Technical Terms. 2nd ed. McGraw-Hill, New York, N.Y.

Moreau, R. A., Norton, R. A. and Hicks, K. B. 1999. Phytosterols and phytostanols lower cholesterol. INFORM 10:572-577.

NRC. 1982. United States-Canadian Tables of Feed Composition. 3rd Rev. Nat. Acad. Press, Washington, D.C.

RFA. 2004. U.S. fuel ethanol production capacity. Renewable Fuels Association. www.ethanolrfa.org/eth_prod_fac.html. December. Washington, D.C.

Singh, V., Moreau, R. A., Hicks, K. B., Belyea, R. L. and Staff, C. H. 2002. Removal of fiber from distillers dried grains with solubles (DDGS) to increase value. Trans. ASAE 45:389-392.

Treybal, R. E. 1980. Mass-transfer operations. 3rd ed. McGraw-Hill, New York, N.Y.

Van Soest, P. J., Robertson, J. B. and Lewis B. A. 1991. Methods for dietary fiber, neutral detergent fiber and non-starch polysaccharides in relation to animal nutrition. J. Dairy Sci. 74:3583-3597. (See Symposium: Carbohydrate methodology, metabolism, and nutritional implications in dairy cattle.)

STATEMENTS REGARDING INCORPORATION BY REFERENCE AND VARIATIONS

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

REFERENCES

Eckhoff, S R et al., 1996, A 100-g laboratory corn wet-milling procedure, Cereal Chem. 73(1):54-57.

Singh V., et al., Modified dry grind ethanol process, Publication of the Agricultural Engineering Department, University of Illinois at Urbana-Champaign, UILU No. 2001-7021; Jul. 18, 2001.

C. C. Huang, Air classifiers: How they work and how to select one; Powder and Bulk Engineering, December 1996.

Moreau R A et al., 1999, Cereal Chemistry 76(3):449-451.

Singh V et al., 2003, Cereal Chemistry 80(2):118-122.

Wu, Y V and Stringfellow A C, 1982, Corn Distillers' Dried Grains with Solubles and corn Distillers' Dried Grains: Dry Fractionation and Composition, Journal of Food Science 47:1155-1157, 1180.

Wu, Y V and Stringfellow, A C, 1986, Simple dry fractionation of Corn Distillers' Dried Grains and Corn Distillers' Dried Grains with Solubles, Cereal Chemistry 63(1):60-61.

Zhang Y, G. L. Riskowski and L. L. Christianson. 1998. Analysis and Development of a Uniflow Aerodynamic Deduster. Final Research Report 878-TRP. Society of Heating, Refrigeration and Air-Conditioning Engineers. 1791 Tullie Circle NE, Atlanta, Ga. 30329.

U.S. Pat. No. 6,254,914 by Singh et al., issued Jul. 3, 2001.

U.S. Patent Application 20030104587 by Verser et al., published Jun. 5, 2003; U.S. Patent Application 20030180415 by Stiefel et al., published Sep. 25, 2003; U.S. Patent Application 20030232109 by Dawley et al., published Dec. 18, 2003.

Feed analysis was performed for certain measurements by a commercial analytical laboratory source, according to which the following references are applicable for a given analysis by type of method.

TABLE 16

References for feed analysis methods.

| Analysis | Type of Method | Reference |
|---|---|---|
| Moisture | Convection Oven | AOAC* 930.15 |
| | Vacuum oven | AOAC 926.07, 925.45 |
| Protein, crude | Combustion (Dumas) | AOAC 990.03 Leco FP 528 |
| Fat, crude | Ether extraction | AOAC 920.39 |
| | Acid hydrolysis | AOAC 954.02 |
| | Alkaline hydrolysis | AOAC 932.06 |
| Fiber | Acid detergent | AOAC 973.18 Ankom |
| | Neutral detergent | NFTA** Ankom |
| | Crude | AOAC 962.09 Ankom |
| | RFV | NFTA |
| Ash | Furnace 600° C. | AOAC 942.05 (1990) |
| Minerals | Wet Ash ICAP | AOAC 985.01M |
| Nitrate | FIA | Alpkem Segmented Flow |
| Salt | Titration AgNO3 | |
| | Calculated from chloride | |
| | ICAP | ICAP-AOAC 985.01 M |
| | Calculated from sodium | |
| Carotene/Vitamin A | HPLC | US FDA F93-4434 |
| Aflatoxin | Screen | Aflatest |
| | Thin layer chromatography | AOAC 975.36 (1990) |

*AOAC = Association of Official Analytical Chemists
**NFTA = National Forage Testing Association

The invention claimed is:

1. A method of generating a fiber-reduced fraction and a fiber-enriched fraction from a distillers dried grains (DDG) or distillers dried grains with solubles (DDGS) material, comprising:
   a) processing corn to produce said DDG or DDGS material;
   b) separating by size said DDG or DDGS material into a first fraction and a second fraction, wherein said first fraction has a larger particle size and said second fraction has a smaller particle size;
   c) collecting said second fraction;
   d) air classifying said first fraction so as to yield a first subfraction of a lighter material enriched in fiber relative to said first fraction and a second subfraction of a heavier material reduced in fiber relative to said first fraction; and
   e) collecting said second subfraction, wherein said second subfraction is reduced in fiber relative to said DDG or DDGS material; thereby generating the fiber-reduced fraction and the fiber-enriched fraction.

2. The method of claim 1 further comprising combining said second fraction of smaller particle size and said second subfraction, thereby forming a combined material reduced in fiber relative to said DDG or DDGS material.

3. The method of claim 2 wherein said combined material has a fiber content of 10% or less.

4. The method of claim 2 wherein said combined material is enriched in protein content, fat content, or both protein and fat content relative to said DDG or DDGS material.

5. The method of claim 1 further comprising a second air classifying by gravity air elutriation of said second fraction of smaller particle size so as to yield a third subfraction of a lighter material enriched in fiber and a fourth subfraction of a heavier material reduced in fiber relative to said second fraction.

6. The method of claim 5 further comprising combining said fourth subfraction and said second subfraction, thereby forming a combined material reduced in fiber relative to said DDG or DDGS material.

7. The method of claim 6 wherein said combined material has increased fat and protein concentration relative to said DDG or DDGS material.

8. The method of claim 5 further comprising combining said first subfraction with said third subfraction, thereby forming a combined material enriched in fiber relative to said DDG or DDGS material.

9. The method of claim 1 wherein said air classifying is gravity air elutriation utilizing an air velocity between approximately 1.59 and 4.45 m/s.

10. The method of claim 1 wherein said air classifying is gravity air elutriation utilizing an air velocity between approximately 2.22 and 2.6 m/s.

11. The method of claim 1 wherein said separating by size is performed by sieving using a pore size between approximately 600 and 850 microns.

12. A method of generating a fiber reduced fraction from a distillers dried grains (DDG) or distillers dried grains with solubles (DDGS) material comprising:
   a) processing corn to produce said DDG or DDGS material;
   b) separating by size said DDG or DDGS material into a first fraction and a second fraction, wherein said first fraction has a larger particle size and said second fraction has a smaller particle size and is reduced in fiber in relation to said DDG or DDGS material;
   c) air classifying said second fraction so as to yield a first subfraction of a lighter material enriched in fiber relative to said second fraction and a second subfraction of a heavier material reduced in fiber relative to said second fraction; and
   d) collecting said second subfraction, wherein said second subfraction is reduced in fiber relative to said DDG or DDGS material; thereby generating the fiber-reduced fraction.

13. The method of claim 12 wherein said collected second subfraction has a fiber content of 10% or less.

14. The method of claim 12 wherein said combined second subfraction has is enriched in protein content, fat content, or both protein and fat content relative to said DDG or DDGS material.

15. The method of claim 12 further comprising air classifying said first fraction using gravity air elutriation so as to yield a third subfraction of a lighter material enriched in fiber and a fourth subfraction of a heavier material reduced in fiber relative to said first fraction.

16. The method of claim 15 further comprising combining said fourth subfraction and said second subfraction, thereby forming a combined material reduced in fiber relative to said DDG or DDGS material.

17. The method of claim 15 further comprising combining said first fraction and said third subfraction, thereby forming a combined material enriched in fiber relative to said DDG or DDGS material.

18. The method of claim 12 wherein said air classifying is gravity air elutriation utilizing an air velocity between approximately 1.59 and 4.45 m/s.

19. The method of claim 12 wherein said air classifying is gravity air elutriation utilizing an air velocity between approximately 2.22 and 2.6 m/s.

20. The method of claim 12 wherein said separating by size is performed by sieving using a pore size between approximately 600 and 850 microns.

21. The method of claim 12 wherein said air classifying step employs an air classification system selected from the group consisting of: static cyclone, cyclone classifiers, single or multi-stage dynamic classifiers, cross-flow classifiers, spiral separators, high energy dispersion classifiers, and turbine classifiers (single and multiple wheel).

* * * * *